(12) United States Patent
Takagi et al.

(10) Patent No.: US 8,183,432 B2
(45) Date of Patent: May 22, 2012

(54) PLANT HAVING REDUCED LIGNIN AND CELLULOSE CONTENTS WITHOUT REDUCING GLUCAN CONTENT, METHOD OF PRODUCING THE SAME AND UTILIZATION THEREOF

(75) Inventors: Masaru Takagi, Tsukuba (JP); Nobutaka Mitsuda, Tsukuba (JP); Akira Iwase, Tsukuba (JP); Keiichiro Hiratsu, Tsukuba (JP)

(73) Assignees: Japan Science and Technology Agency, Saitama (JP); National Institute of Advanced Industrial Science and Technology, Tokyo (JP)

( * ) Notice: Subject to any disclaimer, the term of this patent is extended or adjusted under 35 U.S.C. 154(b) by 523 days.

(21) Appl. No.: 12/280,722

(22) PCT Filed: Feb. 27, 2007

(86) PCT No.: PCT/JP2007/053673
§ 371 (c)(1),
(2), (4) Date: Aug. 26, 2008

(87) PCT Pub. No.: WO2007/102346
PCT Pub. Date: Sep. 13, 2007

(65) Prior Publication Data
US 2009/0019605 A1    Jan. 15, 2009

(30) Foreign Application Priority Data

Feb. 28, 2006 (JP) ............................. 2006-053331
Dec. 22, 2006 (JP) ............................. 2006-346684

(51) Int. Cl.
C12N 15/82   (2006.01)
C12N 15/10   (2006.01)
C12N 15/00   (2006.01)
A01H 5/00    (2006.01)

(52) U.S. Cl. ............... 800/278; 800/295; 435/320.1; 435/468; 536/23.1; 536/23.6; 536/24.2

(58) Field of Classification Search .................. None
See application file for complete search history.

(56) References Cited

U.S. PATENT DOCUMENTS

| | | | |
|---|---|---|---|
| 6,303,847 B1 | 10/2001 | Kawaoka et al. | |
| 6,812,377 B2 | 11/2004 | Chiang et al. | |
| 7,049,481 B1 | 5/2006 | Chiang et al. | |
| 7,232,941 B2 | 6/2007 | Chiang et al. | |
| 7,342,148 B2 | 3/2008 | Takagi et al. | |
| 2002/0078474 A1 | 6/2002 | Chiang et al. | |
| 2002/0123623 A1 | 9/2002 | Kawaoka et al. | |
| 2003/0082511 A1* | 5/2003 | Brown et al. | 435/4 |
| 2004/0045049 A1 | 3/2004 | Zhang et al. | |
| 2005/0183169 A1 | 8/2005 | Takagi et al. | |
| 2006/0206964 A1 | 9/2006 | Chiang et al. | |

FOREIGN PATENT DOCUMENTS

| | | |
|---|---|---|
| EP | 1 469 010 | 10/2004 |
| EP | 1 702 508 | 9/2006 |
| JP | 2001-269176 | 10/2001 |
| JP | 2001-269177 | 10/2001 |
| JP | 2001-269178 | 10/2001 |
| JP | 2001-269179 | 10/2001 |
| JP | 2001-292776 | 10/2001 |
| JP | 2001-292777 | 10/2001 |
| WO | WO 2004045049 | * 4/2004 |
| WO | WO 2005122751 | * 12/2005 |

OTHER PUBLICATIONS

Supplementary European Search Report for corresponding Application No. 07737458.5 dated Aug. 27, 2009.
Database EMBL (Online), Aug. 1, 2003 "SALK_149909.37.05.x Arabidopsis thaliana TDNA insertion lines Arabidopsis thaliana genomic clone SALK_149909.37.05.x, genomic survey sequence", XP002540921, retrieved from EBI accession No. EMBL: CC887284; Database accession No. CC887284.
Database Tair Germplasm/Stock: SALK_149909, Aug. 15, 2003, XP002540922, Database accession No. Germplasm 1005895332.
Database Tair Polymorphism: SALK_149909.37.05.x, Aug. 3, 2003, XP002540923, Database accession No. 1005871746.
International Search Report for corresponding Application No. PCT/JP2007/053673 mailed Apr. 10, 2007.
Alonso JM et al.; "SALK_015495.54.50.x Arabidopsis thaliana TDNA insertion lines Arabidopsis thaliana genomic clone SALK_015495.54.50.x, genomic survey sequence"; [online]; Apr. 2003 uploaded; NCBI Entrez Nucleotide, Accession No. CC052264 (GI: 29471928). Retrieved from Internet: URL: http://wwwncbi.nlm.nih.gov/entrez/viewer/fcgi?db=nucleotide&val=29471928 on Mar. 30, 2007.
Mitsuda N. et al.; "The NAC transcription factors NST1 and NST2 of the Arabidopsis regulate secondary wall thickenings and are required for anther dehiscence"; Plant Cell; 2005; vol. 17, No. 11; pp. 2993-3006.
Mitsuda N. et al.; "NAC transcription factors NST1 and NST3, are key regulators of the formation of secondary walls in woody tissues of Arabidopsis"; Plant Cell; Jan. 2007; vol. 19, No. 1; pp. 270-280.

(Continued)

Primary Examiner — Brent T Page
(74) Attorney, Agent, or Firm — Renner, Otto, Boisselle & Sklar, LLP

(57) ABSTRACT

By inhibiting the function of a transcription factor that promotes transcription of a gene associated with the amounts of lignin and cellulose, a plant in which the amounts of lignin and cellulose are reduced without reducing the amount of glucan is produced. In this plant, glucan in the obtained cell wall components is in the state of highly easily undergoing saccharification. In this plant, moreover, natural dehiscence of pods is suppressed. A method of inhibiting the transcription factor includes a method in which a chimeric gene between a transcription factor gene and a polynucleotide that encodes a functional peptide capable of converting the transcription factor into a transcription repressor is introduced into a plant cell so that a chimeric protein in which the transcription factor is fused with the functional peptide is produced in a plant cell, and a method of inhibiting the expression of the transcription factor, such as knockout method or RNAi method. Thus, a plant in which the amounts of lignin and cellulose are reduced without reducing the amount of glucan is provided.

3 Claims, 12 Drawing Sheets

OTHER PUBLICATIONS

Ohta M. et al.; "Repression Domains of Class II ERF Transcriptional Repressors Share an Essential Motif for Active Repression"; The Plant Cell, Aug. 2001; vol. 13; pp. 1959-1968.

K. Hiratsu et al. ;"The SUPERMAN protein is an active repressor whose carboxy-terminal repression domain is required for the development of normal flowers"; FEBS Letters; 2002; vol. 514; pp. 351-354.

* cited by examiner

PLANT HAVING REDUCED LIGNIN AND CELLULOSE CONTENTS WITHOUT REDUCING GLUCAN CONTENT, METHOD OF PRODUCING THE SAME AND UTILIZATION THEREOF

TECHNICAL FIELD

The present invention relates to a plant in which the amounts of lignin and cellulose are reduced without reducing the amount of glucan, a producing method of the plant, and use of the plant and the producing method. More specifically, the present invention relates to a method of producing a plant in which the amounts of lignin and cellulose are reduced without reducing the amount of glucan by inhibiting the function of a transcription factor that promotes the transcription of a gene associated with the amounts of lignin and cellulose, a plant obtained by the producing method, and use of the plant.

BACKGROUND ART

Ethanol manufactured from biomass is lower alcohol fuel that plays important role in reduction of $CO_2$ emission. Examples of biomass ethanol that has been commercially practical includes the ones obtained by ethanol fermentation of starch sugar from sugarcane, corn, or the like.

Cellulose, which is biomass resource, mainly constitutes lignocellulose (ligneous resource). As with cellulose, lignin is a major component in the support structure of a woody plant. In recent years, attention has been focused on woody biomass such as a woody plant, and research has been made on the technique of efficiently generating glucose from a woody plant and manufacturing ethanol from glucose derived from a woody plant. Especially, the technique of manufacturing monosaccharide or oligosaccharide from lignocellulose composed of cellulose and lignin has been developed.

For the manufacture of paper and/or pulp and the use of lignocellulose as a material for sugars, it is necessary to obtain cellulose by disaggregating or disassembling lignin that firmly bonds to cellulose from lignocellulose. However, enormous amounts of time and cost are required for the disaggregation/disassembly of lignin. As such, there has been demand for the production of trees containing low lignin content.

A technique of modifying lignin content and/or cellulose content in a plant is known. Especially, phenylpropanoid biosynthesis pathway that is lignin biosynthesis pathway has received attention (see Patent Documents 1 and 2, for example). Patent Document 1 discloses that lignin content in a plant is reduced by suppressing the function of a transcription factor promoting the expression of an enzyme that functions in phenylpropanoid biosynthesis pathway. Patent Document 2 discloses a technique of transforming a plant with a plurality of genes derived from phenylpropanoid biosynthesis pathway.

Further, a technique of reducing lignin biosynthesis while increasing cellulose biosynthesis by causing a plant to express an enzyme related to cellulose synthesis pathway is also known (see Patent Document 3).

[Patent Document 1]
Japanese Unexamined Patent Publication No. 276181/1999 (Tokukaihei 11-276181, published on Oct. 12, 1999)
[Patent Document 2]
Japanese PCT National Phase Unexamined Patent Publication No. 515224/2004 (Tokuhyo 2004-515224, published on May 27, 2004)
[Patent Document 3]
Japanese PCT National Phase Unexamined Patent Publication No. 509009/2003 (Tokuhyo 2003-509009, published on Mar. 11, 2003)
[Patent Document 4]
Japanese Unexamined Patent Publication No. 269177/2001 (Tokukai 2001-269177, published on Oct. 2, 2001)
[Patent Document 5]
Japanese Unexamined Patent Publication No. 269178/2001 (Tokukai 2001-269178, published on Oct. 2, 2001)
[Patent Document 6]
Japanese Unexamined Patent Publication No. 292776/2001 (Tokukai 2001-292776, published on Oct. 2, 2001)
[Patent Document 7]
Japanese Unexamined Patent Publication No. 292777/2001 (Tokukai 2001-292777, published on Oct. 23, 2001)
[Patent Document 8]
Japanese Unexamined Patent Publication No. 269176/2001 (Tokukai 2001-269176, published on Oct. 2, 2001)
[Patent Document 9]
Japanese Unexamined Patent Publication No. 269179/2001 (Tokukai 2001-269179, published on Oct. 2, 2001)
[Patent Document 10]
International Publication No. WO03/055903, pamphlet (published on Jul. 10, 2003)
[Patent Document 11]
Japanese Unexamined Patent Publication No. 278422/2005 (Tokukai 2005-278422, published on Oct. 13, 2005)
[Non-Patent Document 1]
Mitsuda, N., Seki, M., Shinozuka, K. and Ohme-Takagi, M., The Plant Cell, Vol. 17, 2993-3006, November, 2005
[Non-Patent Document 2]
Ohta, M., Matsui, K., Hiratsu, K., Shinshi, H. and Ohme-Takagi, M., The Plant Cell, Vol. 13, 1959-1968, August, 2001
[Non-Patent Document 3]
Hiratsu, K., Ohta, M., Matsui, K., Ohme-Takagi, M., FEBS Letters 514 (2002) 351-354

DISCLOSURE OF INVENTION

In order to obtain alcohol fuel from a plant, it is necessary to generate oligosaccharides or monosaccharide by hydrolysis of glycosidic linkage in polysaccharide, such as cellulose, with oxygen or an acid. Therefore, even when lignin content is low in a plant, an additional step is required for hydrolysis of cellulose (i.e. saccharification). Such an additional step is unnecessary if saccharification occurs in a plant.

However, a technique for reducing the amount of crystalline cellulose in a plant without reducing the amount of glucan is not known. Further, in the known technique of modifying lignin content and/or cellulose content, the reduction of lignin content and the increase of cellulose content in a plant (alternatively, the increase of lignin content and the reduction of cellulose content) correlate with each other, and a technique for reducing both lignin content and cellulose content is not known.

The present invention has been attained in view of the above problem, and an object of the present invention is to realize the technique for reducing the amounts of lignin and cellulose without reducing the amount of glucan. As used herein, the "cellulose" the amount of which is reduced in a plant by application of the present invention refers to crystalline cellulose.

The inventors of the present invention diligently worked to solve the foregoing problem and accomplished the present invention by finding that it is possible to reduce the amounts of lignin and cellulose without reducing the amount of glucan, by inhibiting the function of a particular transcription factor. That is, the present invention provides a plant in which the amounts of lignin and cellulose are reduced without reducing the amount of glucan, a producing method of the plant, and a kit for reducing the amounts of lignin and cellulose in a plant without reducing the amount of glucan.

In order to solve the above problem, a producing method of a plant according to the present invention in which amounts of lignin and cellulose are reduced without reducing an amount of glucan comprises the step of: inhibiting a function of a polypeptide having an amino acid sequence represented by SEQ ID NO: 74 in a plant.

In this way, the transcription of a target gene for a transcription factor having the amino acid sequence represented by SEQ ID NO: 74 can be effectively suppressed. As a result, a plant in which the transcription of the gene is effectively suppressed can reduce the amounts of lignin and cellulose without reducing the amount of glucan.

In a producing method of a plant according to the present invention, it is preferable that the step of inhibiting the function of a protein is carried out by causing the plant to produce a fusion protein in which the polypeptide having the amino acid sequence represented by SEQ ID NO: 74 is fused with a functional peptide capable of converting an arbitrary transcription factor into a transcription repressor.

In a producing method of a plant according to the present invention, it is more preferable that the step of inhibiting the function of a protein is carried out by further causing the plant to produce a fusion protein in which a polypeptide having an amino acid sequence represented by SEQ ID NO: 72 is fused with a functional peptide capable of converting an arbitrary transcription factor into a transcription repressor.

In a producing method of a plant according to the present invention, the step of inhibiting the function of a protein may be carried out by causing the plant to express a chimeric DNA in which a polynucleotide having a base sequence represented by SEQ ID NO: 73 is ligated in-frame to a polynucleotide that encodes a functional peptide capable of converting an arbitrary transcription factor into a transcription repressor.

In a producing method of a plant according to the present invention, the step of inhibiting the function of a protein may be carried out by further causing the plant to express a chimeric DNA in which a polynucleotide having a base sequence represented by SEQ ID NO: 71 is ligated in-frame to a polynucleotide that encodes a functional peptide capable of converting an arbitrary transcription factor into a transcription repressor.

In this way, the chimeric protein or a protein encoded by the chimeric DNA can effectively suppress the transcription of a target gene for the transcription factor. As a result, a plant in which the chimeric protein or a protein encoded by the chimeric DNA is produced can reduce the amounts of lignin and cellulose without reducing the amount of glucan.

In a producing method of a plant according to the present invention, it is preferable that the functional peptide has an amino acid sequence represented by any one of:

(1) X1-Leu-Asp-Leu-X2-Leu-X3;
(2) Y1-Phe-Asp-Leu-Asn-Y2-Y3;
(3) Z1-Asp-Leu-Z2-Leu-Arg-Leu-Z3; and
(4) Asp-Leu-Z4-Leu-Arg-Leu, where X1 represents 0 to 10 amino acid residues, X2 represents Asn or Glu, X3 represents at least six amino acid residues, Y1 represents 0 to 10 amino acid residues, Y2 represents Phe or Ile, Y3 represents at least six amino acid residues, Z1 represents Leu, Asp-Leu, or Lue-Asp-Leu, Z2 represents Glu, Gln or Asp, Z3 represents 0 to 10 amino acid residues, and Z4 represents Glu, Gln, or Asp.

In a producing method of a plant according to the present invention, the functional peptide may be a polypeptide having an amino acid sequence represented by any one of SEQ ID NO: 1 through 17.

In a producing method of a plant according to the present invention, the functional peptide may have:

(a) an amino acid sequence represented by SEQ ID NO: 18 or 19; or (b) an amino acid sequence having substitution, deletion, insertion, and/or addition of one to several amino acids in the amino acid sequence represented by SEQ ID NO: 18 or 19.

In a producing method of a plant according to the present invention, the functional peptide may have an amino acid sequence represented by:

(5) α1-Leu-β1-Leu-γ1-Leu where α1 is Asp, Asn, Glu, Gln, Thr, or Ser, β1 is Asp, Gln, Asn, Arg, Glu, Thr, Ser, or His, and γ1 is Arg, Gln, Asn, Thr, Ser, His, Lys, or Asp.

In a producing method of a plant according to the present invention, the functional peptide may have an amino acid sequence represented by any one of:

(6) α1-Leu-β1-Leu-γ2-Leu;
(7) α1-Leu-β2-Leu-Arg-Leu; and
(8) α2-Leu-β1-Leu-Arg-Leu;

where α1 is Asp, Asn, Glu, Gln, Thr, or Ser, α2 is Asn, Glu, Gln, Thr, or Ser, β1 is Asp, Gln, Asn, Arg, Glu, Thr, Ser, or His, β2 is Asn, Arg, Thr, Ser, or His, and γ2 is Gln, Asn, Thr, Ser, His, Lys, or Asp.

In a producing method of a plant according to the present invention, the functional peptide may have an amino acid sequence represented by SEQ ID NO: 117, 120, 123, 126, 129, 132, 135, 138, 141, 144, 147, 150, 153, 156, 159, 162, 171, 174, or 177.

In a producing method of a plant according to the present invention, the functional peptide may have an amino acid sequence represented by SEQ ID NO: 165 or 168.

In a producing method of a plant according to the present invention, it is preferable that the step of inhibiting the function of a protein is carried out by inhibiting expression of the protein in the plant.

In a producing method of a plant according to the present invention, it is preferable that inhibition of the expression is carried out by knockout method or RNAi method.

A plant according to the present invention is produced by the above producing method and has lignin and cellulose the amounts of which are reduced without reducing the amount of glucan.

A plant according to the present invention preferably includes at least one of: an adult plant; a plant cell; a plant tissue; a callus; and a seed.

A kit for reducing amounts of lignin and cellulose in a plant without reducing an amount of glucan according to the present invention, comprises:

(a) a polynucleotide that encodes a functional peptide capable of converting an arbitrary transcription factor into a transcription repressor; and (b) a polynucleotide having a base sequence represented by SEQ ID NO: 73.

A kit according to the present invention may further comprise: (c) a polynucleotide having a base sequence represented by SEQ ID NO: 71.

A kit according to the present invention may further comprise: (d) an expression vector for expressing a polypeptide of interest in a plant.

A kit according to the present invention may further comprise: (e) reagents for introducing the expression vector (d) into plant cells.

It should be noted that in a plant according to the present invention in which the amounts of lignin and cellulose are reduced without reducing the amount of glucan, natural dehiscence of pods is also suppressed. That is, the present invention also provides a plant in which natural dehiscence of pods is suppressed, a producing method of the plant, and a kit for suppressing natural dehiscence of pods in a plant.

In order to solve the above problem, a producing method of a plant according to the present invention in which natural dehiscence of pods is suppressed comprises the step of: inhibiting a function of a polypeptide having an amino acid sequence represented by SEQ ID NO: 74 in a plant.

In this way, the transcription of a target gene for a transcription factor having the amino acid sequence represented by SEQ ID NO: 74 can be effectively suppressed. As a result, in a plant in which the transcription of the gene is effectively suppressed, natural dehiscence of pods can be suppressed.

In a producing method of a plant according to the present invention in which natural dehiscence of pods is suppressed, it is preferable that the step of inhibiting the function of a protein is carried out by causing the plant to produce a fusion protein in which the polypeptide having the amino acid sequence represented by SEQ ID NO: 74 is fused with a functional peptide capable of converting an arbitrary transcription factor into a transcription repressor.

In a producing method of a plant according to the present invention in which natural dehiscence of pods is suppressed, it is more preferable that the step of inhibiting the function of a protein is carried out by further causing the plant to produce a fusion protein in which a polypeptide having an amino acid sequence represented by SEQ ID NO: 72 is fused with a functional peptide capable of converting an arbitrary transcription factor into a transcription repressor.

In a producing method of a plant according to the present invention in which natural dehiscence of pods is suppressed, the step of inhibiting the function of a protein may be carried out by causing the plant to express a chimeric DNA in which a polynucleotide having a base sequence represented by SEQ ID NO: 73 is ligated in-frame to a polynucleotide that encodes a functional peptide capable of converting an arbitrary transcription factor into a transcription repressor.

In a producing method of a plant according to the present invention in which natural dehiscence of pods is suppressed, the step of inhibiting the function of a protein may be carried out by further causing the plant to express a chimeric DNA in which a polynucleotide having a base sequence represented by SEQ ID NO: 71 is ligated in-frame to a polynucleotide that encodes a functional peptide capable of converting an arbitrary transcription factor into a transcription repressor.

In this way, the chimeric protein or a protein encoded by the chimeric DNA can effectively suppress the transcription of a target gene for the transcription factor. As a result, dehiscence of pods can be suppressed in a plant in which the chimeric protein or a protein encoded by the chimeric DNA is produced.

In a producing method of a plant according to the present invention in which natural dehiscence of pods is suppressed, it is preferable that the functional peptide has an amino acid sequence represented by any one of:
 (1) X1-Leu-Asp-Leu-X2-Leu-X3;
 (2) Y1-Phe-Asp-Leu-Asn-Y2-Y3;
 (3) Z1-Asp-Leu-Z2-Leu-Arg-Leu-Z3; and
 (4) Asp-Leu-Z4-Leu-Arg-Leu,
where X1 represents 0 to 10 amino acid residues, X2 represents Asn or Glu, X3 represents at least six amino acid residues, Y1 represents 0 to 10 amino acid residues, Y2 represents Phe or Ile, Y3 represents at least six amino acid residues, Z1 represents Leu, Asp-Leu, or Lue-Asp-Leu, Z2 represents Glu, Gln or Asp, Z3 represents 0 to 10 amino acid residues, and Z4 represents Glu, Gln, or Asp.

In a producing method of a plant according to the present invention in which natural dehiscence of pods is suppressed, the functional peptide may be a polypeptide having an amino acid sequence represented by any one of SEQ ID NO: 1 through 17.

In a producing method of a plant according to the present invention in which natural dehiscence of pods is suppressed, the functional peptide may have:
 (a) an amino acid sequence represented by SEQ ID NO: 18 or 19; or
 (b) an amino acid sequence having substitution, deletion, insertion, and/or addition of one to several amino acids in the amino acid sequence represented by SEQ ID NO: 18 or 19.

In a producing method of a plant according to the present invention in which natural dehiscence of pods is suppressed, the functional peptide may have an amino acid sequence represented by:
 (5) α1-Leu-β1-Leu-γ1-Leu
where α1 is Asp, Asn, Glu, Gln, Thr, or Ser, β1 is Asp, Gln, Asn, Arg, Glu, Thr, Ser, or His, and γ1 is Arg, Gln, Asn, Thr, Ser, His, Lys, or Asp.

In a producing method of a plant according to the present invention in which natural dehiscence of pods is suppressed, the functional peptide may have an amino acid sequence represented by any one of:
 (6) α1-Leu-β1-Leu-γ2-Leu;
 (7) α1-Leu-β2-Leu-Arg-Leu; and
 (8) α2-Leu-1-Leu-Arg-Leu;
where α1 is Asp, Asn, Glu, Gln, Thr, or Ser, α2 is Asn, Glu, Gln, Thr, or Ser, β1 is Asp, Gln, Asn, Arg, Glu, Thr, Ser, or His, β2 is Asn, Arg, Thr, Ser, or His, and γ2 is Gln, Asn, Thr, Ser, His, Lys, or Asp.

In a producing method of a plant according to the present invention in which natural dehiscence of pods is suppressed, the functional peptide may have an amino acid sequence represented by SEQ ID NO: 117, 120, 123, 126, 129, 132, 135, 138, 141, 144, 147, 150, 153, 156, 159, 162, 171, 174, or 177.

In a producing method of a plant according to the present invention in which natural dehiscence of pods is suppressed, the functional peptide may have an amino acid sequence represented by SEQ ID NO: 165 or 168.

In a producing method of a plant according to the present invention in which natural dehiscence of pods is suppressed, it is preferable that the step of inhibiting the function of a protein is carried out by inhibiting expression of the protein in the plant.

In a producing method of a plant according to the present invention in which natural dehiscence of pods is suppressed, it is preferable that inhibition of the expression is carried out by knockout method or RNAi method.

A plant according to the present invention is produced by the above producing method, and natural dehiscence of pods is suppressed in the plant.

A plant according to the present invention preferably includes at least one of: an adult plant; a plant cell; a plant tissue; a callus; and a seed.

A kit according to the present invention for suppressing natural dehiscence of pods in a plant, comprises:
 (a) a polynucleotide that encodes a functional peptide capable of converting an arbitrary transcription factor into a transcription repressor; and
 (b) a polynucleotide having a base sequence represented by SEQ ID NO: 73.

A kit according to the present invention for suppressing natural dehiscence of pods in a plant may further comprise: (c) a polynucleotide having a base sequence represented by SEQ ID NO: 71.

A kit according to the present invention for suppressing natural dehiscence of pods in a plant may further comprise: (d) an expression vector for expressing a polypeptide of interest in a plant.

A kit according to the present invention for suppressing natural dehiscence of pods in a plant may further comprise: (e) reagents for introducing the expression vector (d) into plant cells.

Additional objects, features, and strengths of the present invention will be made clear by the description below. Further, the advantages of the present invention will be evident from the following explanation in reference to the drawings.

BRIEF DESCRIPTION OF DRAWINGS

FIG. 4(*b*) is a view showing pods and their transverse sections of the wild-type *Arabidopsis thaliana* and the mutant *Arabidopsis thaliana* in which NST1 gene and/or NST3 gene were disrupted, which were observed under a microscope (high magnification).

FIG. 5(*b*) is a view showing the result of comparison between the wild-type *Arabidopsis thaliana* and the NST1/NST3 gene disruption plant in terms of glucan content per direct weight.

FIG. 5(*c*) is a view showing the result of comparison between the wild-type *Arabidopsis thaliana* and the NST1/NST3 gene disruption plant in terms of glucan content per dry weight.

FIG. 5(*d*) is a view showing the result of comparison between the wild-type *Arabidopsis thaliana* and the NST1/NST3 gene disruption plant in terms of lignin content per direct weight.

FIG. 5(*e*) is a view showing the result of comparison between the wild-type *Arabidopsis thaliana* and the NST1/NST3 gene disruption plant in terms of lignin content per dry weight.

FIG. 7(*b*) is a view of the result of analysis of the disruption lines, showing that neither NST1 gene nor NST3 gene are expressed in the double gene disruption lines.

FIG. 7(*c*) is a view showing that the formation of xylem is significantly suppressed in inflorescence stem and hypocotyl of the NST1/NST3 double gene disruption line.

FIG. 8(*b*) is a graph showing Young's moduli (strengths of stems) calculated by using the inflorescence stems.

FIG. 8(*c*) is a graph showing the result of x-ray diffraction analysis of the crystal state of cellulose microfibrils that constitute secondary walls in the inflorescence stems of the wild-type line and the NST1/NST3 double gene disruption line.

FIG. 8(*d*) is a graph showing the result of x-ray diffraction analysis of the crystal state of cellulose microfibrils that constitute secondary walls in the inflorescence stems of the wild-type line and the NST1/NST3 double gene disruption line.

FIG. 9(*b*) is a graph showing comparison between the wild-type line and the double gene disruption line in expressions of the genes that encode enzymes involved in synthesis of secondary walls.

FIG. 10(*b*) is a view showing inflorescence stems of the wild-type line, ProNST1:NST1SRDX expression line, ProNST3:NST3SRDX expression line, and ProNST3:NST1SRDX expression line when observed under transmitted light radiation and under ultraviolet radiation.

BEST MODE FOR CARRYING OUT THE INVENTION

Figure 1:
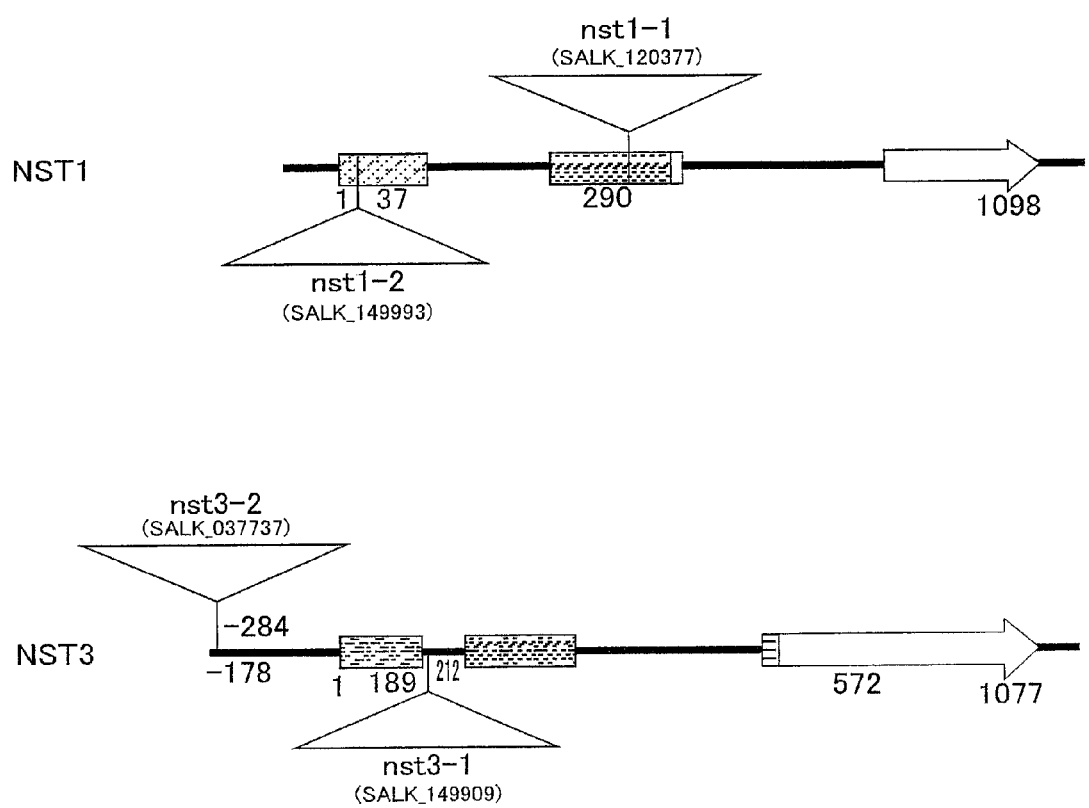
FIG. 1 is a diagram showing the positions where T-DNAs were inserted in NST1 gene and NST3 gene.

The present invention provides: (i) a plant in which the amount of lignin and the amount of cellulose are reduced without reducing the amount of glucan, by inhibition of the function of a gene identified as encoding a transcription factor associated with the amount of lignin and the amount of cellulose in the plant; and (ii) a producing method of the plant. The use of a plant according to the present invention, in which the amount of lignin and the amount of cellulose are reduced without reducing the amount of glucan, facilitates the generation of glucose from a woody plant and thus facilitates the manufacture of ethanol from glucose derived from a woody plant. A plant according to the present invention can be obtained by inhibiting the function of a transcription factor that is encoded by a gene associated with the amount of lignin and the amount of cellulose in the plant.

In one aspect, the present invention provides a producing method of a plant in which the amount of lignin and the amount of cellulose are reduced without reducing the amount of glucan. In one embodiment, a producing method of a plant according to the present invention in which the amount of lignin and the amount of cellulose are reduced without reducing the amount of glucan, can comprise the step of inhibiting the function of polypeptide having an amino acid sequence represented by SEQ ID NO: 74 in the plant.

In another aspect, the present invention provides a plant in which the amount of lignin and the amount of cellulose are reduced without reducing the amount of glucan. In yet another aspect, the present invention provides a kit for reducing the amount of lignin and the amount of cellulose without reducing the amount of glucan.

As used herein, the term "transcription factor" means a polypeptide that positively or negatively controls transcription or initiation reaction of the transcription (transcription control factor), and preferably means a polypeptide that positively controls transcription or initiation reaction of the transcription. That is, the expression "inhibiting the function of a transcription factor" means causing loss of the function of the transcription control factor. The loss of the function of the transcription control factor includes, for example, loss of protein-to-protein interaction capability, loss of DNA binding capability, and loss and/or reversal of the transcription control function. A person skilled in the art who reads the specification can easily understand that a transcription factor losing these functions is in a state where the functions thereof are inhibited. A method for inhibiting the function of a transcription factor may be a method of inhibiting the synthesis of RNA or a method of inhibiting the synthesis of a protein.

As used herein, the term "polypeptide" is used interchangeably with "peptide" or "protein". A "fragment" of the polypeptide refers to a partial fragment of the polypeptide. A polypeptide according to the present invention may be isolated from a natural source or chemically synthesized.

By "isolated" polypeptide or protein is intended a polypeptide or a protein removed from its natural environment. For example, recombinantly produced polypeptides and proteins expressed in host cells are considered isolated for purposes of the invention as are native or recombinant polypeptides and proteins which have been substantially purified by any suitable technique.

The "polypeptides" include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the "polypeptides" may be glycosylated or may be non-glycosylated. In addition, "polypeptides" may also include an initial modified methionine residue, in some cases as a result of host-mediated processes.

The "polypeptide" is not particularly limited as long as it is made up of amino acids bonded together by peptide bonding. The polypeptide may be a conjugate polypeptide that includes a non-polypeptide structure. As used herein, the "non-polypeptide structure" refers to a sugar chain or an isoprenoid group, for example. However, the meaning of the term is not particularly limited.

A gene that is associated with the amount of lignin and the amount of cellulose in a plant both of which are controlled by a polypeptide having an amino acid sequence represented by SEQ ID NO: 74 or a polypeptide having an amino acid sequence represented by SEQ ID NO: 72 according to the present invention has not been revealed.

As used herein, the polypeptide having the amino acid sequence represented by SEQ ID NO: 74 can be used interchangeably with NST3 protein or NST3 polypeptide. A polynucleotide having a base sequence represented by SEQ ID NO: 73 can be used interchangeably with NST3 gene. The polypeptide having the amino acid sequence represented by SEQ ID NO: 72 can be used interchangeably with NST1 protein or NST1 polypeptide, and a polynucleotide having a base sequence represented by SEQ ID NO: 71 can be used interchangeably with NST1 gene.

The present invention further provides (i) a plant in which natural dehiscence of pods is suppressed by inhibition of the function of a gene identified as encoding a transcription factor associated with natural dehiscence of pods and (ii) a producing method of the plant. The use of a plant of the present invention in which natural dehiscence of pods is suppressed facilitates the harvesting of pods having mature seeds therein and an efficient harvesting of seeds contained in the pods.

The plant of the present invention in which natural dehiscence of pods is suppressed can be obtained by inhibition of the function of a transcription factor that is encoded by a gene associated with natural dehiscence of pods.

In one aspect, the present invention provides a producing method of a plant in which natural dehiscence of pods is suppressed. In one embodiment, a producing method of a plant according to the present invention in which natural dehiscence of pods is suppressed can comprise the step of inhibiting the function of a polypeptide having the amino acid sequence represented by SEQ ID NO: 74 in the plant. In another aspect, the present invention provides a plant in which natural dehiscence of pods is suppressed. In still another aspect, the present invention provides a kit for suppressing natural dehiscence of pods in a plant.

As used herein, the term "natural dehiscence of pods" means that pods of a wild plant or a mutant plant are split due to maturity of their seeds and drying of the pods and the seeds contained in the pod are therefore exposed to the outside. Release of the seeds may or may not occur due to the natural dehiscence of pods.

A gene that is associated with natural dehiscence of pods controlled by a polypeptide having the amino acid sequence represented by SEQ ID NO: 74 or SEQ ID NO: 72 according to the present invention has not been revealed. However, it is indicated that a target gene of the polypeptide having the amino acid sequence represented by SEQ ID NO: 72 is a gene that expresses an enzyme or the like involved in lignin synthesis in various kinds of tissues, including a pod, anther, and stems (see Non-Patent Document 1). As will be described later in Examples, the polypeptide having the amino acid sequence represented by SEQ ID NO: 74 or the polypeptide having the amino acid sequence represented by SEQ ID NO: 72 according to the present invention positively controls lignin synthesis in pods, anther, and inflorescence stems. It is known that pods contract by undergoing lignification and dehydration at valve endodermal layer and a site called valve margin. From the above, it is considered that the two polypeptides are transcription factors that positively control lignin synthesis.

(I) Method of Converting a Transcription Factor into a Transcription Repressor

The following will describe a method of reducing the amount of lignin and the amount of cellulose without reducing the amount of glucan in a plant or a method of suppressing natural dehiscence of pods, by causing a plant to produce a chimeric protein of the present invention, in which a transcription factor that promotes transcription of a gene associated with the amount of lignin and the amount of cellulose in a plant or a gene associated with natural dehiscence of pods in a plant is fused with a functional peptide that converts a transcription factor into a transcription repressor. It should be noted that a chimeric protein in which a transcription factor of interest is fused with a functional peptide that converts the transcription factor into a transcription repressor is herein also referred to as "chimeric repressor".

(I-1) Chimeric Protein Used in the Present Invention

As described previously, a chimeric protein used in the present invention is a protein in which a transcription factor that promotes transcription of a gene associated with the amount of lignin and the amount of cellulose in a plant is fused with a functional peptide that converts an arbitrary transcription factor into a transcription repressor. Furthermore, the chimeric protein used in the present invention, which is capable of suppressing natural dehiscence of pods, can be said to be a protein in which a transcription factor that promotes transcription of a gene associated with natural dehiscence of pods is fused with a functional peptide that converts an arbitrary transcription factor into a transcription repressor. The "functional peptide that converts an arbitrary transcription factor into a transcription repressor" will be described in detail in Section (I-3).

Further, a chimeric protein used in the present invention acts dominantly over endogenous genes. Specifically, a chimeric protein according to the present invention exhibits the same repressing action on the expression of a gene associated with the amount of lignin and the amount of cellulose in a plant or a gene associated with natural dehiscence of pods, regardless of whether the plant is a diploid or an amphiploid, or the plant have functionally redundant genes. Thus, by introducing a gene that encodes the above chimeric protein, it is possible to effectively produce a plant in which the amount of lignin and the amount of cellulose are reduced without reducing the amount of glucan (or a plant in which natural dehiscence of pods is suppressed).

(I-2) Transcription Factor that Promotes Transcription of a Gene Associated with the Amounts of Lignin and Cellulose in a Plant or a Gene Associated with Natural Dehiscence of Pods in a Plant The transcription factor used in producing a plant in which the amounts of lignin and cellulose are reduced without reducing the amount of glucan is not limited to the protein (polypeptide) having the amino acid sequence represented by SEQ ID NO: 74 or SEQ ID NO: 72 as long as it is a transcription factor that promotes transcription of a gene associated with the amounts of lignin and cellulose in a plant. Further, the transcription factor used in producing a plant in which natural dehiscence of pods is suppressed is not limited to the protein (polypeptide) having the amino acid sequence represented by SEQ ID NO: 74 or SEQ ID NO: 72 as long as it is a transcription factor that promotes transcription of a gene associated with natural dehiscence of pods. Specifically, in any cases, a protein with the substitution, deletion, insertion, and/or addition of one to several amino acids in the amino acid sequence represented by SEQ ID NO: 74 or SEQ ID NO: 72 can be used in the present invention as long as it has the foregoing function. Referring to the phrase "substitution, deletion, insertion, and/or addition of one to several amino acids," the number of amino acids substituted, deleted, inserted, and/or added in the amino acid sequence of SEQ ID NO: 74 or SEQ ID NO: 72 is not particularly limited. For example, the number of amino acids is 1 to 20, preferably 1 to 10, more preferably 1 to 7, further preferably 1 to 5, and particularly preferably 1 to 3.

The transcription factor also includes a protein sharing not less than 50%, preferably not less than 60% or 70% homology with the amino acid sequence represented by SEQ ID NO: 74 or SEQ ID NO: 72, and that is capable of promoting transcription of a gene associated with the amounts of lignin and cellulose in a plant or a gene associated with natural dehiscence of pods in a plant. As used herein, the term "homology" refers to the proportion of the same amino acid sequence. The higher the homology, the closer the relationship between the two.

Concerning the transcription factor that promotes transcription of a gene associated with the amounts of lignin and cellulose in a plant, the amino acid sequence of the transcription factor used in the present invention is believed to be highly conserved in plants of many different species. As such, the transcription factor or a gene that encodes the transcription factor is not necessarily required to be isolated from each individual plant for which suppression of the amount of lignin and the amount of cellulose or suppression of natural dehiscence of pods is desired. That is, a gene that encodes a chimeric protein constructed in *Arabidopsis thaliana*, as will be described later, is introduced into other plants, whereby it is possible to easily produce plants in which the amount of lignin and the amount of cellulose are reduced without reducing the amount of glucan (plants in which natural dehiscence of pods is suppressed) in a wide range of plant species.

For the production of a chimeric protein used in the present invention, conventional genetic recombination techniques can be suitably used, as will be described later. Thus, a plant producing method according to the present invention can suitably use a gene that encodes the transcription factor.

The gene that encodes the transcription factor is not particularly limited as long as it corresponds to the amino acid sequence of the transcription factor based on the genetic code. When the transcription factor is the protein having the amino acid sequence represented by SEQ ID NO: 74, a specific example is a gene that encodes the same protein. For example, the transcription factor is a polynucleotide that has the base sequence of SEQ ID NO: 73 as an open reading frame (ORF).

The polynucleotide having the base sequence represented by SEQ ID NO: 73 used in the present invention, or the coding gene of the transcription factor is not just limited to the foregoing example. For example, a homologue of a gene having the base sequence of SEQ ID NO: 73 may be used. A specific example is a gene that hybridizes under stringent conditions with a gene of a base sequence complementary to the base sequence of SEQ ID NO: 73, and that encodes the transcription factor. Note that, as used herein, "hybridize under stringent conditions" means binding under washing conditions of 2×SSC at 60° C.

Hybridization can be performed by conventional methods, for example, according to the procedure described in J. Sambrook et al. Molecular Cloning, A Laboratory Manual, 2nd Ed., Cold Spring Harbor Laboratory (1989). As a rule, the level of stringency increases (more difficult to hybridize) with increase in temperature and decrease in salt concentration.

The method by which the coding gene of the transcription factor is obtained is not particularly limited, and the gene can be isolated from a wide variety of plants by conventional methods. For example, a primer pair that has been constructed based on the base sequence of a known transcription factor can be used. With such a primer pair, the gene can be obtained by PCR, for example, using the cDNA or genomic DNA of a plant as a template. Alternatively, the coding gene of the transcription factor can be chemically synthesized by conventional methods.

(I-3) Functional Peptide for Converting a Transcription Factor into a Transcription Repressor A functional peptide for converting a transcription factor into a transcription repressor (will be referred to as "transcription repressor converting peptide" for convenience of explanation) is not particularly limited, as long as it can form a chimeric protein with the transcription factor and thereby suppress transcription of target genes controlled by the transcription factor. Specifically, the transcription repressor converting peptide found by the inventors of the present invention can be used, for example (see, for example, Patent Documents 4 to 10, Non-Patent Documents 2 and 3).

The inventors of the present invention have found that some members of *Arabidopsis thaliana* proteins AtERF3, AtERF4, AtERF7, and AtERF8, which belong to the class II ERF genes, exhibit a notable gene transcription suppressing effect when they are bound to the transcription factor. Base on this finding, the inventors constructed effecter plasmids that include (i) coding genes of these proteins and (ii) DNA excised from these genes. By inserting these effecter plasmids into plant cells, gene transcription was successfully suppressed (see Patent Documents 4 to 7, for example). The same experiment was carried out with genes that encode tobacco ERF3 protein (see Patent Document 8, for example) and rice OsERF3 protein (see Patent Document 9, for example), which belong to the class II ERF genes; and genes that encode *Arabidopsis thaliana* ZAT10 and *Arabidopsis thaliana* ZAT11, which belong to the zinc finger protein genes. Gene transcription was successfully suppressed in all of these experiments. The inventors have also found that these proteins shared a common motif of aspartic acid-leucine-asparagine (DLN) in a C terminus region. A further study of the proteins having such a common motif revealed that the protein that suppresses gene transcription can be a peptide of a very simple structure, and that a peptide of such a simple structure is indeed capable of converting a transcription factor into a transcription repressor.

Further, the inventors have also found that *Arabidopsis thaliana* SUPERMAN protein does not share the common motif, yet is capable of converting a transcription factor into a transcription repressor. It was also found that a chimeric gene in which a coding gene of the SUPERMAN protein is bound to a DNA binding domain of the transcription factor or a coding gene of the transcription factor serves as a strong transcription repressor.

Thus, in the present embodiment, examples of transcription repressor converting peptides used in the present invention include: class II ERF *Arabidopsis thaliana* proteins such as AtERF3, AtERF4, AtERF7, and AtERF8; tobacco ERF3 protein and rice OsERF3 protein, which are also members of class II ERF proteins; zinc finger proteins such as *Arabidopsis thaliana* ZAT10, *Arabidopsis thaliana* ZAT11, and SUPERMAN protein; peptides excised from these proteins; and synthetic peptides having the foregoing functions.

As used herein, the term "functional peptide" means a peptide which can convert a transcription factor into a transcription repressor, and can be used interchangeably with "transcription repressor converting peptide" or "repressor domain".

In one embodiment, the functional peptide preferably has the amino acid sequence as defined by any one of the following Formulae (I) through (4), for example:

(1) X1-Leu-Asp-Leu-X2-Leu-X3;
(2) Y1-Phe-Asp-Leu-Asn-Y2-Y3;
(3) Z1-Asp-Leu-Z2-Leu-Arg-Leu-Z3; and
(4) Asp-Leu-Z4-Leu-Arg-Leu (where X1 represents 0 to 10 amino acid residues, X2 represents Asn or Glu, X3 represents at least six amino acid residues, Y1 represents 0 to 10 amino acid residues, Y2 represents Phe or Ile, Y3 represents at least six amino acid residues, Z1 represents Leu, Asp-Leu, or Lue-Asp-Leu, Z2 represents Glu, Gln or Asp, Z3 represents 0 to 10 amino acid residues, and Z4 represents Glu, Gln, or Asp.)

In the functional peptide of Formula (1), X1 represents 0 to 10 amino acid residues. The type of amino acid constituting the amino acid residue represented by X1 is not particularly limited. In other words, the functional peptide of Formula (1) may include one amino acid of any kind or an oligomer of 2 to 10 amino acid residues of any kind attached to the N terminus, or no amino acid may be attached at all.

For ease of synthesis of the functional peptide of Formula (1), the amino acid residues represented by X1 should be as short as possible. Preferably, the number of amino acid residues represented by X1 should be 10 or less, or more preferably 5 or less.

Further, in the functional peptide of Formula (1), X3 represents at least six amino acid residues. The type of amino acid constituting the amino acid residue represented by X3 is not particularly limited. In other words, the functional peptide of Formula (1) may include an oligomer of six or more amino acid residues of any kind attached to the C terminus. The number of amino acid residues represented by X3 needs to be at least six to exhibit the foregoing functions.

In the functional peptide of Formula (1), the pentamer (5 mer) of five amino acid residues, excluding X1 and X3, has the sequence as represented by SEQ ID NO: 20 or 21. The pentamer has the amino acid sequence of SEQ ID NO: 20 when X2 is Asn and the amino acid sequence of SEQ ID NO: 21 when X2 is Glu.

In the functional peptide of Formula (2), Y1 represents 0 to 10 amino acid residues as does X1 in the functional peptide of Formula (1). The type of amino acid constituting the amino acid residue represented by Y1 is not particularly limited. In other words, the functional peptide of Formula (2) may include one amino acid of any kind or an oligomer of 2 to 10 amino acid residues of any kind attached to the N terminus, or no amino acid may be attached at all.

For ease of synthesis of the functional peptide of Formula (2), the amino acid residues represented by Y1 should be as short as possible. Preferably, the number of amino acid residues should be 10 or less, or more preferably 5 or less.

Further, in the functional peptide of Formula (2), Y3 represents at least six amino acid residues as does X3 in the functional peptide of Formula (1). The type of amino acid constituting the amino acid residue represented by Y3 is not particularly limited. In other words, the functional peptide of Formula (2) may include an oligomer of six or more amino acid residues of any kind attached to the C terminus. The number of amino acid residues represented by Y3 needs to be at least six to exhibit the foregoing functions.

In the functional peptide of Formula (2), the pentamer (5 mer) of five amino acid residues, excluding Y1 and Y3, has the sequence as represented by SEQ ID NO: 22 or 23. The pentamer has the amino acid sequence of SEQ ID NO: 22 when Y2 is Phe and the amino acid sequence of SEQ ID NO: 23 when Y2 is Ile. The tetramer (4 mer) of four amino acid residues, excluding Y2, has the sequence represented by SEQ ID NO: 82.

In the functional peptide of Formula (3), the amino acid residues represented by Z1 include 1 to 3 amino acids, including Leu. Z1 is Leu when the number of amino acids is one, Asp-Leu when the number of amino acids is two, and Lue-Asp-Leu when the number of amino acids is three.

In the functional peptide of Formula (3), Z3 represents 0 to 10 amino acid residues, as does X1 in the functional peptide of Formula (1) for example. The type of amino acid constituting the amino acid residue represented by Z3 is not particularly limited. In other words, the functional peptide of Formula (3) may include one amino acid of any kind or an oligomer of 2 to 10 amino acid residues of any kind attached to the C terminus, or no amino acid may be attached at all.

For ease of synthesis of the functional peptide of Formula (3), the amino acid residues represented by Z3 should be as short as possible. Preferably, the number of amino acid residues should be 10 or less, or more preferably 5 or less. Non-limiting examples of amino acid residues represented by Z3 include Gly, Gly-Phe-Phe, Gly-Phe-Ala, Gly-Tyr-Tyr, and Ala-Ala-Ala.

The total number of amino acid residues in the functional peptide of Formula (3) is not particularly limited. However, for ease of synthesis, the total number of amino acid residues is preferably 20 or less.

In the functional peptide of Formula (3), the oligomer of 7 to 10 amino acid residues, excluding Z3, has the sequence as represented by SEQ ID NO: 24 to 32. The oligomer has the amino acid sequence of SEQ ID NO: 24, 25, or 26 when Z1 is Leu and Z2 is Glu, Gln, or Asp, respectively. The oligomer has the amino acid sequence of SEQ ID NO: 27, 28, or 29 when Z1 is Asp-Leu and Z2 is Glu, Gln, or Asp, respectively. The oligomer has the amino acid sequence of SEQ ID NO: 30, 31, or 32 when Z1 is Leu-Asp-Leu and Z2 is Glu, Gln, or Asp, respectively.

The functional peptide of Formula (4) is a hexamer (6 mer) of six amino acid residues, and it has the amino acid sequence of SEQ ID NO: 5, 14, or 33. The hexamer has the amino acid sequence of SEQ ID NO: 5 when Z4 is Glu, the amino acid sequence of SEQ ID NO: 14 when Z4 is Asp, and the amino acid sequence of SEQ ID NO: 33 when Z4 is Gln.

The functional peptide used in the present invention may be a peptide that has, for example, the hexamer of Formula (4) as the smallest sequence. For example, the amino acid sequence of SEQ ID NO: 5 corresponds to the sequence of amino acids 196 to 201 of *Arabidopsis thaliana* SUPERMAN protein (SUP protein), and it is a sequence which the inventors of the present invention have found to be the functional peptide.

In the present embodiment, it is more preferable that the functional peptide is a peptide having any one of the amino acid sequences of SEQ ID NO: 1 through 17.

It is confirmed that the oligopeptides having the amino acid sequences of SEQ ID NO: 1 through 17 are the functional peptides, by subjecting the synthesized peptides to the methods disclosed in Patent Documents 5 through 10, and Non-Patent Documents 2 and 3.

Further, it is confirmed that the oligopeptides having the amino acid sequences of SEQ ID NO: 1 and 4 are the functional peptides, by the fact that such oligopeptides are ligated to EIN3 gene encoding a transcription factor of a plant to transform *Arabidopsis thaliana* plant.

Similarly, it is confirmed that the oligopeptide having the amino acid sequence represented by SEQ ID NO: 16 is the functional peptide, by the fact that such an oligopeptide is ligated to CUC1 gene encoding a transcription factor of a plant to transform *Arabidopsis thaliana* plant.

Similarly, it is confirmed that the oligopeptide having the amino acid sequence represented by SEQ ID NO: 17 is the functional peptide, by the fact that such an oligopeptide is ligated to PAP1 gene or AtMYB23 encoding a transcription factor of a plant to transform *Arabidopsis thaliana* plant.

In the present embodiment, the functional peptides more preferably have:
(a) the amino acid sequence represented by SEQ ID NO: 18 or 19; or
(b) an amino acid sequence having the substitution, deletion, insertion, and/or addition of one to several amino acids in the amino acid sequence represented by SEQ ID NO: 18 or 19.

Referring to the phrase "substitution, deletion, insertion, and/or addition of one to several amino acids," the number of amino acids substituted, deleted, inserted, and/or added in the amino acid sequence of SEQ ID NO: 18 or 19 is not particularly limited. For example, the number of amino acids is 1 to 20, preferably 1 to 10, more preferably 1 to 7, further preferably 1 to 5, and particularly preferably 1 to 3.

The deletion, substitution, or addition of amino acid can be brought about by modifying the base sequence that encodes the peptide, using a method known in the art. The base sequence can be mutated by a conventional method, such as the Kunkel method or Gapped duplex method, or methods according to these techniques. For example, mutation can be introduced with a mutation introducing kit employing site-specific mutagenesis (for example, Mutant-K or Mutant-G (TAKARA)), or the LA PCR in vitro Mutagenesis series kit (TAKARA).

The functional peptide is not just limited to a peptide with the total length sequence of the amino acid sequence represented by SEQ ID NO: 18, and it may be a peptide with a partial sequence of the amino acid sequence of SEQ ID NO: 18.

An example of such a peptide with a partial sequence is a peptide with the amino acid sequence (amino acid 175 to 204 of the amino acid sequence of SUP protein) represented by SEQ ID NO: 19. Another example is the peptide represented by Formula (3).

In another embodiment, the functional peptide preferably has the amino acid sequence represented by the following Formula (5):

(5) α1-Leu-β1-Leu-γ1-Leu
where α1 is Asp, Asn, Glu, Gln, Thr, or Ser, β1 is Asp, Gln, Asn, Arg, Glu, Thr, Ser, or His, and γ1 is Arg, Gln, Asn, Thr, Ser, His, Lys, or Asp.

The peptide represented by Formula (5) is classified into peptides of amino acid sequences represented by the following Formulae (6) through (9):

(6) α1-Leu-β1-Leu-γ2-Leu;
(7) α1-Leu-β2-Leu-Arg-Leu; or
(8) α2-Leu-β1-Leu-Arg-Leu;
(9) Asp-Leu-β3-Leu-Arg-Leu;
where α1 is Asp, Asn, Glu, Gln, Thr, or Ser, α2 is Asn, Glu, Gln, Thr, or Ser, β1 is Asp, Gln, Asn, Arg, Glu, Thr, Ser, or His, β2 is Asn, Arg, Thr, Ser, or His, β3 is Glu, Asp, or Gln, and γ2 is Gln, Asn, Thr, Ser, His, Lys, or Asp.

In the present embodiment, it is more preferable that the functional peptide can be a peptide having the amino acid sequence represented by SEQ ID NO: 117, 120, 123, 126, 129, 132, 135, 138, 141, 144, 147, 150, 153, 156, 159, 162, 171, 174, or 177. Among these peptides, the peptide of SEQ ID NO: 138, 141, 147, 153, 171, 174, or 177 corresponds to the peptide represented by General Formula (6). The peptide of SEQ ID NO: 117, 126, 156, 159, or 162 corresponds to the peptide represented by General Formula (7). The peptide of SEQ ID NO: 129, 132, 135, 144, or 150 corresponds to the peptide represented by General Formula (8). The peptide of SEQ ID NO: 120 or 123 corresponds to the peptide represented by General Formula (9).

Further, in the present embodiment, it is more preferable that the functional peptide can be a peptide having the amino acid sequence represented by SEQ ID NO: 165 or 168.

It is confirmed that the peptide having the amino acid sequence represented by SEQ ID NO: 117, 120, 123, 126, 129, 132, 135, 138, 141, 144, 147, 150, 153, 156, 159, 162, 171, 174, or 177 are the functional peptides by the following method. First of all, a polynucleotide that encodes each of the peptides (base sequence of the polynucleotide will be described later) is synthesized, and the synthesized polynucleotide is then ligated to a coding region of DNA-binding domain of GAL4 transcription factor of yeast and further ligated to the downstream side of a cauliflower mosaic virus 35S promoter that becomes functional in a plant cell, so as to construct an effecter plasmid. Separately, a reporter gene realized by luciferase gene is constructed in which an enhancer region of a cauliflower mosaic virus 35S promoter, GAL4 protein-binding DNA sequence, and a TATA region of a cauliflower mosaic virus 35S promoter are ligated to a promoter region of a cauliflower mosaic virus 35S promoter. The effecter plasmid and the reporter gene are introduced into a leaf of *Arabidopsis thaliana* by using a gene gun (particle gun) at once. Then, it is possible to examine whether to be the functional peptide or not by measuring the activity of the luciferase gene that is the reporter gene.

The polynucleotide (transcription repressor converting polynucleotide) that encodes the functional peptide is not particularly limited as long as it includes a base sequence that, based on the genetic code, corresponds to the amino acid sequence of the functional peptide.

An example of the transcription repressor converting polynucleotide includes a polynucleotide having the base sequence represented by SEQ ID NO: 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 118, 119, 121, 122, 124, 125, 127, 128, 130, 131, 133, 134, 136, 137, 139, 140, 142, 143, 145, 146, 148, 149, 151, 152, 154, 155, 157, 158, 160, 161, 163, 164, 166, 167, 169, 170, 172, 173, 175, 176, 178, or 179.

The peptide of SEQ ID NO: 1 is encoded by the polynucleotide having the base sequence of SEQ ID NO: 83 or 84, the peptide of SEQ ID NO: 2 is encoded by the polynucleotide having the base sequence of SEQ ID NO: 85 or 86, the peptide of SEQ ID NO: 3 is encoded by the polynucleotide having the base sequence of SEQ ID NO: 87 or 88, the peptide of SEQ ID NO: 4 is encoded by the polynucleotide having the base sequence of SEQ ID NO: 89 or 90, the peptide of SEQ ID NO: 5 is encoded by the polynucleotide having the base sequence of SEQ ID NO: 91 or 92, the peptide of SEQ ID NO: 6 is encoded by the polynucleotide having the base sequence of SEQ ID NO: 93 or 94, the peptide of SEQ ID NO: 7 is encoded by the polynucleotide having the base sequence of SEQ ID NO: 95 or 96, the peptide of SEQ ID NO: 8 is encoded by the polynucleotide having the base sequence of SEQ ID NO: 97 or 98, the peptide of SEQ ID NO: 9 is encoded by the polynucleotide having the base sequence of SEQ ID NO: 99 or 100, the peptide of SEQ ID NO: 10 is encoded by the polynucleotide having the base sequence of SEQ ID NO: 101 or 102, the peptide of SEQ ID NO: 11 is encoded by the polynucleotide having the base sequence of SEQ ID NO: 103 or 104, the peptide of SEQ ID NO: 12 is encoded by the polynucleotide having the base sequence of SEQ ID NO: 105 or 106, the peptide of SEQ ID NO: 13 is encoded by the polynucleotide having the base sequence of SEQ ID NO: 107 or 108, the peptide of SEQ ID NO: 14 is encoded by the polynucleotide having the base sequence of SEQ ID NO: 109 or 110, the peptide of SEQ ID NO: 15 is encoded by the polynucleotide having the base sequence of SEQ ID NO: 111 or 112, the peptide of SEQ ID NO: 16 is encoded by the polynucleotide having the base sequence of SEQ ID NO: 113 or 114, the peptide of SEQ ID NO: 17 is encoded by the polynucleotide having the base sequence of SEQ ID NO: 115 or 116, the peptide of SEQ ID NO: 117 is encoded by the polynucleotide having the base sequence of SEQ ID NO: 118 or 119, the peptide of SEQ ID NO: 120 is encoded by the polynucleotide having the base sequence of SEQ ID NO: 121 or 122, the peptide of SEQ ID NO: 123 is encoded by the polynucleotide having the base sequence of SEQ ID NO: 124 or 125, the peptide of SEQ ID NO: 126 is encoded by the polynucleotide having the base sequence of SEQ ID NO: 127 or 128, the peptide of SEQ ID NO: 129 is encoded by the polynucleotide having the base sequence of SEQ ID NO: 130 or 131, the peptide of SEQ ID NO: 132 is encoded by the polynucleotide having the base sequence of SEQ ID NO: 133 or 134, the peptide of SEQ ID NO: 135 is encoded by the polynucleotide having the base sequence of SEQ ID NO: 136 or 137, the peptide of SEQ ID NO: 138 is encoded by the polynucleotide having the base sequence of SEQ ID NO: 139 or 140, the peptide of SEQ ID NO: 141 is encoded by the polynucleotide having the base sequence of SEQ ID NO: 142 or 143, the peptide of SEQ ID NO: 144 is encoded by the polynucleotide having the base sequence of SEQ ID NO: 145 or 146, the peptide of SEQ ID NO: 147 is encoded by the polynucleotide having the base sequence of SEQ ID NO: 148 or 149, the peptide of SEQ ID NO: 150 is encoded by the polynucleotide having the base sequence of SEQ ID NO: 151 or 152, the peptide of SEQ ID NO: 153 is encoded by the polynucleotide having the base sequence of SEQ ID NO: 154 or 155, the peptide of SEQ ID NO: 156 is encoded by the polynucleotide having the base sequence of SEQ ID NO: 157 or 158, the peptide of SEQ ID NO: 159 is encoded by the polynucleotide having the base sequence of SEQ ID NO: 160 or 161, the peptide of SEQ ID NO: 162 is encoded by the polynucleotide having the base sequence of SEQ ID NO: 163 or 164, the peptide of SEQ ID NO: 165 is encoded by the polynucleotide having the base sequence of SEQ ID NO: 166 or 167, the peptide of SEQ ID NO: 168 is encoded by the polynucleotide having the base sequence of SEQ ID NO: 169 or 170, the peptide of SEQ ID NO: 171 is encoded by the polynucleotide having the base sequence of SEQ ID NO: 172 or 173, the peptide of SEQ ID NO: 174 is encoded by the polynucleotide having the base sequence of SEQ ID NO: 175 or 176, and the peptide of SEQ ID NO: 177 is encoded by the polynucleotide having the base sequence of SEQ ID NO: 178 or 179.

As required, the transcription repressor converting polynucleotide may include a base sequence that serves as a ligation site for the transcription factor gene. Further, in the case where there is no registration of reading frames between the functional peptide and the transcription factor gene, the transcription repressor converting polynucleotide may additionally include a base sequence for registering the reading frames.

A specific example of the base sequence of the transcription repressor converting polynucleotide including the additional base sequence is the base sequence represented by SEQ ID NO: 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, or 67.

Further, specific examples of the base sequences of the polynucleotides that encode the amino acid sequences represented by SEQ ID NO: 18 and 19 are, for example, the base sequences represented by SEQ ID NO: 68 and 69, respectively.

A chimeric protein used in the present invention can be obtained from the chimeric gene in which the coding gene of the transcription factor is ligated to the transcription repressor converting polynucleotide. As such, the structure of the chimeric protein is not particularly limited as long as it includes a transcription factor site and a transcription repressor converting peptide site. For example, the chimeric protein may include various types of additional polypeptides, such as a polypeptide for linking the transcription factor and the transcription repressor converting peptide, and a polypeptide, such as His, Myc, or Flag, for epitope-labeling the chimeric protein. Further, the chimeric protein may optionally include a non-polypeptide structure, for example, such as a sugar chain and an isoprenoid group.

(II) Knockout Method

As a producing method of a plant according to the present invention in which the amount of lignin and the amount of cellulose are reduced without reducing the amount of glucan (or plant in which natural dehiscence of pods is suppressed), the following will describe knockout method in which mRNA transcription of a desired gene is inhibited by genetically modifying a genome of an individual.

As used herein, the "knockout method" means a method of introducing any one of the following mutations: "deletion of a portion or a whole of DNA sequence of a target DNA" in which "mRNA transcription of a target gene does not occur"; "substitution of a portion or a whole of the DNA sequence of the target DNA with a foreign DNA sequence"; or "insertion of a foreign DNA sequence into a portion or a whole of the DNA sequence of the target DNA". Thus, the function of a transcription factor of interest can be inhibited by a conventional genetic engineering method, such as mutation by homologous recombination, insertion of an activated transposon into a genomic DNA, or insertion of a foreign gene into a genomic DNA.

A mutation introduction technique with respect to a gene used in the present invention is a technique by which mutation can be introduced into a gene, and can be any of various conventional techniques (e.g. treatment by a chemical agent (ethylmethane sulfonate etc.), ultra-violet radiation, or a genetic engineering technique (substitution, insertion, and/or addition of bases by recombination or the like)). However, it is difficult to selectively introduce a desired mutation into a genomic DNA of a plant.

A method for easy and reliable screening for a plant in which a desired mutation is introduced into a desired DNA sequence from among plants in which mutations are introduced at random, may be Targeting Induced Local Lesions IN Genomes (hereinafter referred to as TILLING) method. The following will describe a method for screening for a plant in which a desired mutation (mutation for inhibiting the function of a transcription factor) is introduced into a gene used in the present invention, by using the TILLING method. The TILLING method may be carried out with reference to a known document (Slade A J and Knauf V C, (2005), Transgenic Res.).

A technique by which mutation is randomly introduced to a genome of a seed or a pollen of *Arabidopsis thaliana* will be described below, taking a case using ultraviolet irradiation among the above techniques as an example. A seed into which mutation is introduced by ultraviolet radiation (if mutation is introduced into a pollen, a seed obtained by pollination of such a pollen) is sowed and grown. An obtained first generation (M1) is in a chimeric state having different genomes in respective sections or cells. By self-pollination of M1, a second generation (M2) is produced having identical genomes in all of the cells. Next, a third generation (M3) is produced by self-pollination of M2, and then a seed of M3 is collected. In this case, TILLING library can be obtained by collecting genomic DNAs extracted from M2 individuals in group of 4 to 8 genomic DNAs.

Next, a pair of PCR primers are designed for both ends of at least one desired region in the gene used in the present invention. The primers are labeled with respectively different dyes that emit fluorescence by exposure to excitation light having a particular wavelength. For examples, the dyes can be a combination of Cy3 and Cy5. Cy3 emits fluorescence by exposure to excitation light having a wavelength of about 490 nm, and Cy5 emits fluorescence by exposure to excitation light having a wavelength of about 680 nm. The dyes are not limited to the combination of Cy3 and Cy5 as long as they emit fluorescence by exposure to excitation light beams of respectively different wavelengths. The desired region may have a full length of the gene. In this case, insertion, substitution, or deletion mutation in which termination codon is inserted in-frame on the ORF is preferable. Further, the desired region may be a region that exists on the upstream side of the gene associated with transcription of the gene. However, the desired region is not limited to the above regions as long as it inhibits the function of the transcription factor encoded by the gene due to the presence of mutation in the region.

With the use of the above primers, the desired regions of the genomic DNAs included in the TILLING library are amplified by PCR. In a case where genomic DNAs derived from an individual having mutation in the desired region are included in the DNAs to be amplified by PCR, the amplification brings about the mixture of a heteroduplex of (i) a DNA having mutation and (ii) a normal DNA at a given rate.

The DNAs obtained by amplification are treated with a purified single strand specific endonuclease CELL (see Oleykowski et al., (1998), Nucleic Acids Res, 26: 4597-4602). As a result, the heteroduplex of the DNA having mutation and the normal DNA is cut at a mismatching site, and two fragments are therefore generated. The same samples of a DNA including the two fragments are applied to two gels, and electrophoresed by LI-COR analyzer (LI-COR. Ltd). The electrophoresed two gels are exposed to excitation light beams having respectively different wavelengths so that the labeled primers can be visually identified. For example, assume that Cy3 and Cy5 are used for labeling of the primers. In this case, excitation light having a wavelength of about 490 nm or 680 nm can be used.

For example, in a case where a genomic DNA derived from the individual having mutation in the desired region is included in the DNAs obtained after the PCR amplification, fragments shorter than a fragment whose length is equal to that of the region for which the primers are set are detected from both of the gels. Further, a total length of the fragments detected from the two gels is identical with the length of the region for which the primers are set. Then, a group is determined in which a total length of the two DNA fragments obtained by endonuclease treatment is identical with the length of the region for which the primers are set. By decoding of a base sequence of the desired region in each individual included in the determined group, screening for individuals having mutation in the desired region can be realized.

It should be noted that in a case where a genomic DNA obtained from a group which includes no individuals having mutation in the desired region is amplified by PCR, it is likely to occur that fragments shorter than a fragment whose length is equal to that of the region for which the primers are set are detected from both of the gels. However, it is less likely to occur that a total length of the fragments detected from the two gels is identical with the length of the region for which the primers are set.

The above describes a method of screening a plant in which a desired mutation (mutation for inhibiting the function of a transcription factor) is introduced into a gene used in the present invention, by using the TILLING method. However, a plant screening method according to the present invention is not limited to this and may be any of various conventional methods, as long as a plant in which a desired mutation is introduced into a desired DNA can be screened from among plants into which mutations are introduced at random.

(III) RNAi Method

A technique which is applied to a producing method of a plant according to the present invention in which the amount of lignin and the amount of cellulose are reduced without reducing the amount of glucan (or plant in which natural dehiscence of pods is suppressed), may be any of conventional genetically modifying techniques (e.g. antisense method, sense (cosuppression) method, RNAi method). In the RNAi method, a double stranded RNA (dsRNA) is transcribed to inhibit the synthesis of proteins. The following will describe the RNAi method in which dsRNA is transcribed in a plant.

(III-1) Polynucleotide Used in the RNAi Method

In a case where the expression of a polynucleotide including the base sequence represented by SEQ ID NO: 73 as an open reading is suppressed by using the RNAi method, a target polynucleotide can be a polynucleotide having the base sequence represented by SEQ ID NO: 73, a polynucleotide that hybridizes under stringent conditions with a polynucleotide having a base sequence complementary to the base sequence of SEQ ID NO: 73, or the like. Each of the above polynucleotides encodes the transcription factor having the amino acid sequence represented by SEQ ID NO: 74. As used herein, "hybridize under stringent conditions" means binding under washing conditions of 2×SSC at 60° C. Further, in a case where the expression of a polynucleotide including the base sequence represented by SEQ ID NO: 71 as an open reading is suppressed by using the RNAi method, a target polynucleotide can be a polynucleotide having the base sequence represented by SEQ ID NO: 71, a polynucleotide that hybridizes under stringent conditions with a polynucleotide having a base sequence complementary to the base sequence of SEQ ID NO: 71, or the like. Each of the above polynucleotides encodes the transcription factor having the amino acid sequence represented by SEQ ID NO: 72.

The polynucleotide that can be used in the RNAi method is not particularly limited as long as it includes at least arbitrary 21 consecutive bases in the target polynucleotide, and the number of bases is large enough to suppress the transcription of the target polynucleotide. Further, the polynucleotide that can be used in the RNAi method is not particularly limited as long as it includes at least arbitrary 21 consecutive bases in the sequence complementary to the sequence of the target polynucleotide, and the number of bases is large enough to suppress the transcription of the target polynucleotide.

There may be partial mismatches between a base sequence of a DNA fragment in forward direction and the base sequence complementary to the above region and between a base sequence of a DNA fragment in reverse direction and the base sequence complementary to the above region. A percentage of the mismatches is preferably not more than 5%, more preferably 1 to 3%, further preferably not more than 1%.

Two DNA fragments that are complementary to each other are connected to each other in reversed positions, so that a hairpin structure is formed after transcription. In this case, a spacer region consisting of 100 to 1000 bases for easy cloning may be inserted between the two DNA fragments complementary to each other. A sequence of the spacer region preferably is a sequence of an intron region of arbitrary gene, more preferably a sequence of an intron region of a plant-derived gene.

(III-2) Producing Method of dsRNA

The polynucleotide obtained by connecting the complementary two DNA fragments, which have been described in Section (III-1), in reversed positions is introduced into a plant cell, so that dsRNA can be produced. A specific example of a method of introducing the polynucleotides into plant cells will be described in detail in Section (IV) below.

(IV) Plant Producing Method according to the Present Invention

A plant producing method according to the present invention only needs to include the step of inhibiting the function of the transcription factor. Inclusion of such a step makes it possible to reduce the amount of lignin and the amount of cellulose without reducing the amount of glucan in a plant, and further to suppress natural dehiscence of pods in a plant. More specifically, a plant producing method according to the present invention can include, for example, (1) a mutation introducing step and a screening step, or (2) an expression vector constructing step, a transforming step, and a screening step. The producing method (1) according to the present invention is the method as previously described in Section (II). The following will specifically describe the steps of the plant producing method (2) of the present invention.

(IV-1) Expression Vector Constructing Step

The expression vector constructing step included in the present invention is not particularly limited as long as it includes the step of constructing a recombinant expression vector that includes: a coding gene of the transcription factor described in Section (I-1); the transcription repressor converting polynucleotide described in Section (I-4); and a promoter. Alternatively, the dsRNA expression vector constructing step in the present invention is not particularly limited as long as it includes the step of constructing a recombinant expression vector that includes: the polynucleotide described in Section (III-1); and a promoter.

As the carrier vector of the recombinant expression vector, various types of conventional vectors can be used. Some of the examples include a plasmid, a phage, and a cosmid, which are suitably selected according to the type of plant cell or introducing method. More specific examples are pBR322, pBR325, pUC19, pUC119, pBluescript, pBluescriptSK, and vectors of the pBI family. Binary vectors of the pBI family are preferable when the *Agrobacterium* method is used to introduce the vector into a plant. Specific examples of pBI binary vectors include pBIG, pBIN19, pBI101, pBI121, and pBI221.

The promoter is not particularly limited as long as it can express the gene in plants, and conventional promoters can be suitably used. Examples of the promoter include cauliflower mosaic virus 35S promoter (CaMV35S), actin promoter, a promoter for nopaline synthetase, tobacco PR1a gene promoter, and a promoter with small subunits of tomato ribulose-1,5-biphosphate carboxylase/oxydase. Among these examples, cauliflower mosaic virus 35S promoter and actin promoter can be suitably used. With these promoters, the resulting recombinant expression vector inserted in plant cells can strongly express the gene of interest.

Further, for natural dehiscence of pods, the promoter may be a promoter that can specifically express a gene in valve endodermal layer and/or valve margin of a pod. Examples of such promoters include IND promoter, SHP1 promoter, SHP2 promoter, and ALC promoter. With these promoters, the coding gene of the chimeric protein or the gene that transcribes dsRNA can be expressed only in pods and natural dehiscence of pods can be suppressed without affecting other tissues. With such promoter, the gene can be expressed at a specific time and in a specific tissue, making it possible to more effectively suppress natural dehiscence of pods.

Among the promoters that function in a wide range of plant tissues, the promoter used in the present invention, i.e. the promoter that changes only a trait regarding natural dehiscence of pods (e.g. suppression of secondary wall thickenings in pods or suppression of lignin synthesis) without changing the other traits when the chimeric gene is expressed the dsRNA is transcribed, can be very suitably used in the present invention.

The promoter is not particularly limited as long as (i) it is ligated to be able to express a chimeric gene in which a coding gene of the transcription factor is ligated to the transcription repressor converting polynucleotide, and (ii) it is introduced in the vector. That is, the promoter, as a recombinant expression vector, is not particularly limited to a specific structure. Alternatively, the promoter is not particularly limited as long as (i) it is ligated to be able to transcribe dsRNA, and (ii) it is introduced in the vector. That is, the promoter, as a recombinant expression vector, is not particularly limited to a specific structure.

In addition to the promoter and the chimeric gene, the recombinant expression vector may include other DNA segments. Examples of the other DNA segments include, but are not particularly limited to, terminators, selection markers, enhancers, and base sequences for improving translation efficiency. Further, the recombinant expression vector may additionally include a T-DNA region. With the T-DNA region, the efficiency of gene transfer can be improved, particularly when *Agrobacterium* is used to introduce the recombinant expression vector into plants.

The terminator is not particularly limited and conventional terminators can be used as long as it serves as a transcription termination site. A transcription termination region (Nos terminator) of a nopaline synthetase gene, and a transcription termination region of cauliflower mosaic virus 35S (CaMV35S terminator) can be suitably used, for example. The Nos terminator is more preferably used.

With the terminator suitably placed in the transformation vector, the transformation vector introduced into the plant cell does not cause syntheses of unnecessarily long transcripts, or there will be no reduction in the number of plasmid copies in the presence of a strong promoter.

As the selection marker, a chemical-resistant gene can be used, for example. Specific examples of chemical-resistant genes are those resistant to hygromycin, bleomycin, kanamycin, gentamicin, and chloramphenicol. With such chemical-resistant genes, plants glowing in an antibiotic culture medium can easily be screened for transformants.

As the base sequence for improving translation efficiency, a tobacco mosaic virus omega sequence can be used, for example. With the omega sequence placed in an untranslated region (5' UTR) of the promoter, the translation efficiency of the chimeric gene can be improved. As described so far, the transformant vector may contain various types of DNA segments depending on its purpose.

The method of constructing the recombinant expression vector is not particularly limited. The promoter, the coding gene of the transcription factor, the transcription repressor converting polynucleotide, and optional other DNA segments are introduced in a predetermined order into a suitably selected carrier vector. For example, the coding gene of the transcription factor is ligated to the transcription repressor converting polynucleotide to construct a chimeric gene. The chimeric gene is then ligated to a promoter (and optionally a terminator, etc.) to construct an expression cassette that is inserted into a vector. Also in the case of using RNAi method, the method of constructing the recombinant expression vector is not particularly limited. The promoter, the polynucleotide in which two complementary DNA fragments are connected in reversed positions, and the optional other DNA segments are introduced in a predetermined order into a suitably selected carrier vector. For example, the two complementary DNA fragments are connected in reversed positions. The resulting gene is then ligated to a promoter (and optionally a terminator, etc.) to construct an expression cassette that is inserted into a vector.

In constructing the chimeric gene or the polynucleotide in which two complementary DNA fragments are connected in reversed positions and the expression cassette, the order of DNA segments can be regulated by, for example, having complementary ends at the excision sites of each DNA segment, and then by causing the reaction with a ligase. In the case where the expression cassette contains a terminator, the DNA segments are ordered such that the promoter, the chimeric gene, and the terminator are placed in this order from the upstream side. Further, the type of chemical (e.g. restriction enzyme or ligase) used to construct the recombinant expression vector is not particularly limited, and may be suitably selected from commercially available products.

Further, the proliferation method (producing method) of the recombinant expression vector is not particularly limited and conventional methods can be used. Generally, *E. coli* is used as a host, and the recombinant expression vector is grown therein. In this case, the type of *E. coli* can be suitably selected according to the type of vector used.

(IV-2) Transforming Step

In a transforming step included in the present invention, the recombinant expression vector described in Section (V-1) is introduced into plant cells to produce the chimeric protein described in Section (I) or dsRNA described in Section (III-1).

The method by which the recombinant expression vector is introduced into plant cells (transforming method) is not particularly limited, and conventional method can be suitably used according to the type of plant cell. Specifically, a method using *Agrobacterium*, or a method by which the recombinant expression vector is directly introduced in a plant cell can be used. As an example, a method using *Agrobacterium*, *Transformation of Arabidopsis thaliana by vacuum infiltration* is available.

As examples of a method by which the recombinant expression vector is directly introduced into plant cells, the following methods are available: a micro injection method, an electroporation method, a polyethylene glycol method, a particle gun method, a protoplast fusion method, and a calcium phosphate method.

The plant cell to which the recombinant expression vector is introduced may be, for example, a cell, a callus, or a suspension culture cell of various tissues of plant organs such as a flower, a leaf, and a root.

In a plant producing method according to the present invention, the recombinant expression vector may be suitably selected according to the type of plant to be produced. Alternatively, a multi-purpose recombinant expression vector may be constructed in advance and introduced into plant cells. That is, a plant producing method according to the present invention may or may not contain the recombinant expression vector constructing step described in Section (IV-1).

(IV-3) Screening Step

The screening step included in the present invention only needs to collect individuals in which the production of the chimeric protein described in Section (I) or the dsRNA described in Section (IV) or the introduction of the recombinant vector described in Section (V-1) has been confirmed.

The expression of a protein, the transcription of mRNA, or the introduction of a gene can be confirmed by using various kinds of conventional methods. A method by which the expression of a protein is confirmed may be, for example, Western blotting, in which a desired protein is detected by using an antibody capable of binding specifically to the desired protein. Further, a method by which the transcription of mRNA is confirmed may be Northern blotting, in which detection is performed by using a probe having a sequence complementary to a portion of a desired mRNA. Still further, the introduction of a gene into an individual is confirmed by performing PCR with primers set for a base sequence of a desired polynucleotide.

Apart from the methods listed above, any conventional method can be included as the screening step of the present invention as long as it can confirm the expression of a protein, the transcription of mRNA, or the introduction of a gene in an individual plant.

(V) Plants Obtained by the Present Invention, Usefulness and Use of the Plants

In a plant producing method according to the present invention, the function of the foregoing transcription factor is inhibited in plants. The inhibition of the function of the transcription factor suppresses the expression of target genes that are possibly associated with the amount of lignin and the amount of cellulose in plants. As a result, the amount of lignin and the amount of cellulose can be reduced in plants without reducing the amount of glucan. Alternatively, the inhibition of the function of the transcription factor suppresses the expression of target genes that are possibly associated with natural dehiscence of pods. As a result, natural dehiscence of pods can be suppressed. Thus, the present invention also includes plants that are produced by a plant producing method of the present invention.

(V-1) Plants According to the Present Invention (V-1-1) Plants in which the Amount of Lignin and the Amount of Cellulose are Reduced Without Reducing the Amount of Glucan Plants according to the present invention are not particularly limited to specific kinds, as long as usefulness of the plants can be improved by reduction of the amount of lignin and the amount of cellulose without reducing the amount of glucan. The plants are preferably woody plants and may be needle-leaved trees or broad-leaved trees. Examples of needle-leaved trees include pine, cedar, and cypress. Examples of broad-leaved trees include poplar and eucalyptus.

(V-1-2) Plants in which Natural Dehiscence of Pods is Suppressed

*Leguminosae* plants, *Pedaliaceae* plants, *Violaceae* plants, and other plants form pods containing seeds. When dried, the pods contract and dehisce. When further dried, the pods split open. The seeds in the pods are released by taking advantage of a force exerted when the pods split open.

A pod can be classified into (i) a section composed of cells having primary walls and (ii) a section composed of cells having primary walls and secondary walls. In the process of drying the pods, there is difference in contraction rate between the sections (i) and (ii). The difference in contraction rate causes a tension required for natural dehiscence of pods.

In the natural environment, natural dehiscence of pods is essential for increase of the number of plants and increase of habitats of the plants. However, in a case where plants are grown as commercial products to harvest seeds, it is inconvenient that seeds are released by natural dehiscence of pods. To realize harvesting of seeds before release of the seeds, it is necessary to determine a harvesting time of the seeds by frequently observing pods or by empirically predicting the harvesting time. However, enormous efforts and time are required for frequent observation of the pods, and it is difficult to predict the harvesting time because the degree of maturity of the seeds and the period in which natural dehiscence of pods occurs vary every year due to various weather conditions. In addition, since the degree of maturity of the seeds and the period in which natural dehiscence of pods occurs vary in individual plants, the harvesting cannot be carried out at once. Therefore, it is necessary to carry out harvesting many times even when the best initiation time for harvesting can be determined.

If it is possible to harvest mature seeds before dehiscence of pods, it is unnecessary to consider release of the seeds due to natural dehiscence of pods. This allows a yield of the seeds to be increased. Further, in a case where pods containing seeds are harvested, it is possible to prevent loss of commercial values, which loss occurs due to natural dehiscence of pods. Thus, if plants in which natural dehiscence of pods is suppressed are developed, the above inconvenience resulting from natural dehiscence of pods can be considered to be solved.

For the solution to the above defect, breeding improvement is carried out to develop plants in which natural dehiscence of pods is suppressed. Such a breeding improvement has already achieved success in some plants, and cultivation of the plants has been realized in a large scale. However, there are very few plants of which breeding improvement and commercial production have achieved success.

As a method for producing superior varieties in a short period, a method of interbreeding different varieties of a plant to produce superior varieties in the hybrid crops is commonly employed today. This method takes advantage of heterosis in which interbreeding of different varieties of a plant produces hybrids that have superior traits to the parents. However, although the hybrids that have superior traits to the parents are produced by interbreeding of different varieties of a plant, there is a drawback that children of the hybrids are likely to have inferior traits to the parents of the hybrids.

The inventors of the present invention specified a gene associated with dehiscence of anther in *Arabidopsis thaliana*, and found that the gene promotes secondary wall thickening, which is unique to plant cells, and the secondary wall thickening is essential for dehiscence of anther (see Patent Document 11 and Non-Patent Document 1). Control of dehiscence of anther is as useful as control of natural dehiscence of pods. By using the technique disclosed in Patent Document 11 etc., it is possible to easily suppress dehiscence of anther without complex gene recombination.

For secondary wall thickening, it can be considered that the use of the technique disclosed in Patent Document 11 etc. enables suppression of natural dehiscence of pods. However, natural dehiscence of pods was not completely suppressed, but slightly suppressed in a plant in which the function of the gene disclosed in Patent Document 11 was suppressed. In addition, the frequency of the suppression was low so that the technique disclosed in Patent Document 11 could be regarded as a desired breeding improvement technique.

As described previously, the inventors of the present invention identified the transcription factor that promotes transcription of a gene associated with natural dehiscence of pods, and found that natural dehiscence of pods is suppressed by inhibiting the function of the transcription factor.

Plants according to the present invention in which natural dehiscence of pods is suppressed are not particularly limited to specific kinds, as long as usefulness of the plants can be improved by suppressed natural dehiscence of pods. The plants may be monocots or dicots. Examples of dicots include *Brassicaceae* plants such as *Arabidopsis thaliana*, *Leguminosae* plants, and *Violaceae* plants. Examples of monocots include *Liliaceae* plants such as green onion, Chinese chive, and lily, and *Orchidaceae* plants.

Further, plants according to the present invention in which natural dehiscence of pods is suppressed may be plants whose pods containing seeds or seeds have commercial values, or house plants (flower plants) which themselves have commercial values. Thus, examples of plants according to the present invention in which natural dehiscence of pods is suppressed include: food plants such as soy beans, French beans, red beans, sesame seeds, rapeseeds, vanilla beans, asparagus, cabbage, Chinese cabbage, broccoli, and house plants such as violet, lily, and orchid.

(V-2) Usefulness of Plants According to the Present Invention

Plants according to the present invention in which the amount of lignin and the amount of cellulose are reduced without reducing the amount of glucan are described herein in detail. As such, the following will describe usefulness of plants in which natural dehiscence of pods is suppressed.

The present invention is useful in areas where suppression of natural dehiscence of pods in plants has certain values. The following will describe some of the specific examples; however, usefulness of the present invention is not just limited to the examples described below.

With the technique of the present invention, plants can be produced in which natural dehiscence of pods is suppressed, and breed improvement of food plants can be performed. Plants of the present invention in which natural dehiscence of pods is suppressed do not release seeds from pods. This can increase yields of plants whose seeds and pods containing seeds therein have a commercial value. Further, such plants can be harvested after maturity of their seeds, which allows the plants to be harvested at once.

(V-3) Use of Plants According to the Present Invention

The applicable field or use of plants according to the present invention is not particularly limited. For example, the present invention can be used to provide a kit for performing the plant producing method of the present invention, i.e., a kit for reducing the amount of lignin and the amount of cellulose in plants without reducing the amount of glucan, or a kit for suppressing natural dehiscence of pods in plants.

The present invention can provide a kit for reducing the amount of lignin and the amount of cellulose in plants without reducing the amount of glucan, or a kit for suppressing natural dehiscence of pods in plants. A kit according to the present invention comprises: (a) a polynucleotide that encodes a functional peptide capable of converting an arbitrary transcription factor into a transcription repressor; and (b) a polynucleotide having the base sequence represented by SEQ ID NO: 73. A kit according to the present invention may further comprise: (c) a polynucleotide having the base sequence represented by SEQ ID NO: 71; (d) an expression vector for expressing a polypeptide of interest in a plant; and/or (e) chemicals for introducing the expression vector (d) into plant cells.

In one specific example, the kit according to the present invention at least includes a recombinant expression vector that includes a chimeric gene of (i) a coding gene of the transcription factor and (ii) the transcription repressor converting polynucleotide. More preferably, the kit according to the present invention includes chemicals for introducing the recombinant expression vector into plant cells. Examples of such chemicals include enzymes and buffers, which are selected according to the type of transformation. Optionally, experimental equipment such as a micro centrifugal tube may be included as well.

EXAMPLES

Example 1

Production of NST1/NST3 Gene Disruption Plant

In the present example, (i) seeds of plants in which the function of a transcription factor encoded by NST1 gene of *Arabidopsis thaliana* was disrupted (NST1 T-DNA-TAG LINES: SALK__120377 and SALK__149993) and (ii) seeds of a plant in which the function of a transcription factor encoded by NST3 gene of *Arabidopsis thaliana* was disrupted (NST3 T-DNA-TAG LINE: SALK__149909) were obtained from T-DNA-tagged lines (T-DNA insertion mutant lines) produced by the SALK INSTITUTE in U.S.A.

FIG. 1 is a schematic diagram illustrating the positions where T-DNAs were inserted in gene sequences of SALK__120377, SALK__149993, and SALK__149909. With the T-DNAs inserted at the positions of the respective gene sequences, NST 1 loses the function of a transcription factor in SALK__120377 and SALK__149993, and NST3 also loses the function of a transcription factor in SALK__149909.

In all of the seeds of the plants of three kinds, homozygous plants and heterozygous plants are mixed. For identification of homozygous plants, the seeds of the plants of three kinds were sown and grown, and genomic DNAs were extracted from rosette leaves of the grown plants. In order to perform PCR, primers LBa1 (atggttcacgtagtgggccatc: SEQ ID NO: 75), S120377LP (caaaatcgagattgtgatgtaaaa: SEQ ID NO: 76), and S120377RP (cggacaatctcaagtgcctcc: SEQ ID NO: 77) were designed for the genomic DNA extracted from SALK__120377. Further, the primer LBa1 and primers S149993LP (ttacggggcctactcttttc: SEQ ID NO: 78) and S149993RP (taaaccttgaatgtcccaagg: SEQ ID NO: 79) were designed for the genomic DNA extracted from SALK__149993, and the primer LBa1 and primers S149909LP (cgtattgtttgtagagccgtg: SEQ ID NO: 80) and S149909RP (gtctcgtcgagtcctaccacc: SEQ ID NO: 81) were designed for the genomic DNA extracted from SALK__149909. With the extracted genomic DNAs as templates, PCR was carried out using the following primer pairs: (1) LBa1 (SEQ ID NO: 75) and S120377LP (SEQ ID NO: 76); (2) S120377LP (SEQ ID NO: 76) and S120377RP (SEQ ID NO: 77); (3) LBa1 (SEQ ID NO: 75) and S149993LP (SEQ ID NO: 78); (4) S149993LP (SEQ ID NO: 78) and S149993RP (SEQ ID NO: 79); (5) LBa1 (SEQ ID NO: 75) and S149909LP (SEQ ID NO: 80); or (6) S149909LP (SEQ ID NO: 80) and S149909RP (SEQ ID NO: 81). These primers were designed so as to be located at the corresponding positions on the genomic sequence shown in Table 1 below.

TABLE 1

| Names of Primers | Relative Positions on Sequence* |
|---|---|
| S120377LP | 884 → 861 |
| S120377RP | 33 → 53 |
| S149993LP | −814 → −794 |
| S149993RP | 192 → 172 |
| S149909LP | 814 → 834 |
| S149909RP | −142 → −122 |

*Relative positions on sequence refers to relative positions on genomic sequence when the first A of the initiation codon of NST1 or NST3 is +1.

LBa1 (SEQ ID NO: 75) is recommended as a primer for confirmation of insertion of T-DNA. All of the PCR primers can be designed by WEB application which is provided by the SALK INSTITUTE.

PCR was carried out under the following conditions: denaturation reaction at 95° C. for 2 minutes; 35 cycles each consisting of denaturation reaction at 95° C. for 45 seconds, annealing reaction at 55° C. for 45 seconds, and extension reaction at 72° C. for 45 seconds; and another extension reaction at 72° C. for 7 minutes. All of the PCRs in Examples were carried out under the same conditions.

As a result of the PCR, the SALK_120377 plant that amplified with the primer pair (1) but did not amplify with the primer pair (2) is homozygous plant. As a result of the PCR, the SALK_149993 plant that amplified with the primer pair (3) but did not amplify with the primer pair (4) is homozygous plant. Further, as a result of the PCR, the SALK_149909 plant that amplified with the primer pair (5) but did not amplify with the primer pair (6) is homozygous plant.

SALK_120377 plant with mutation inserted in NST1 gene and SALK_149909 plant with mutation in NST3 gene, both of which were identified as homozygous plant by the PCR, were crossed. By self-pollination of next-generation plants (F1) produced by the crossing, next-generation plants (F2) of F1 were produced. For identification of homozygous plant in which T-DNAs were inserted in alleles of both NST1 gene and NST3 gene in the plants F2, PCR was carried out using the primer pairs (1), (2), (5), and (6). The plants that amplified with the primer pair (1) and the primer pair (5) but did not amplify with the primer pairs (2) and (6) were identified as homozygous plant. The above-produced plants in which T-DNAs were inserted in alleles of both NST1 gene and NST3 gene are referred to as NST1/NST3 gene disruption plants (NST1/NST3 double gene disruption lines), Example 2

Effects of Transcription Factor NST1 or Transcription Factor NST3 on Synthesis of Lignin For comparison between the effects of a transcription factor NST1 and a transcription factor NST3 on the synthesis of lignin, the following plants were grown: wild-type *Arabidopsis thaliana* (represented by wt in FIGS. 2 through 5 and Table 2) as a control; SALK_120377 (represented by nst1 in FIGS. 2 through 4) that was a plant in which the function of NST1 was disrupted; SALK_149909 (represented by nst3 in FIGS. 2 through 4) that was a plant in which the function of NST3 was disrupted; and the NST1/NST3 gene disruption plant (represented by nst1/nst3 in FIGS. 2 through 5 and Table 2) that was a plant in which both of the functions of NST1 and NST3 were disrupted. Comparison between the plants was made in terms of the degree of growth and the amount of lignin in inflorescence stems and hypocotyls of the plants.

Figure 2:
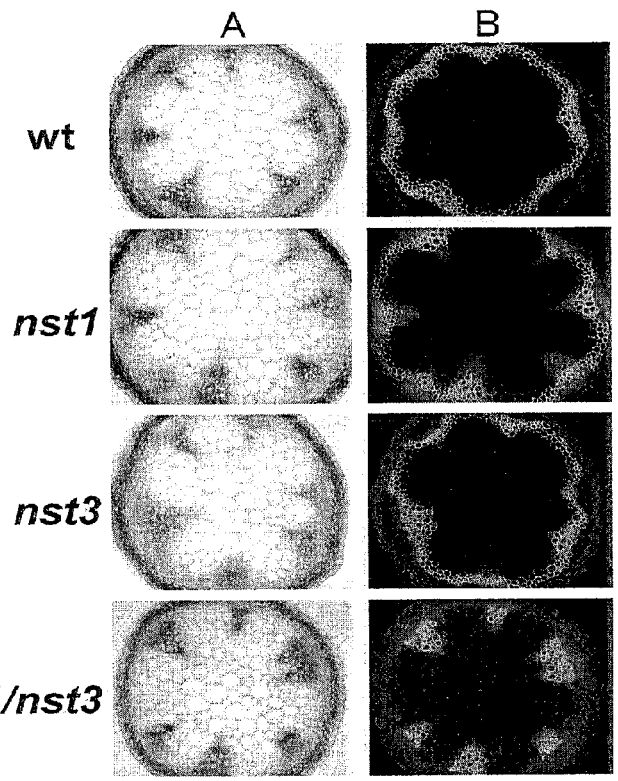
FIG. 2 is cross-sectional views of inflorescence stems of wild-type *Arabidopsis thaliana* and mutant *Arabidopsis thaliana* in which NST1 gene and/or NST3 gene were disrupted, which inflorescence stems were observed under a microscope.

FIG. 2 shows photomicrographs (line A) of inflorescence stem slices of the four plants and photomicrographs (line B) of the same slices in which lignin is visualized, taking advantage of the characteristics of lignin that it emits violet fluorescence upon exposure to ultraviolet rays.

In all of the photographs on line A, outer walls of the inflorescence stems were observed as clear outermost layers, and secondary walls (xylem) of the inflorescence stems were observed as layers immediately inside and along the outer walls of the inflorescence stems and were more vague than the outer walls, vascular bundles of the inflorescence stems were observed in the form of projections extending outward from an inside point. In all of the photographs in line B, the area where lignin was synthesized was brighter than the other area and formed tiny bubbles (FIG. 2).

As shown on line B in FIG. 2, lignin involved in the formation of secondary walls (xylem) of the inflorescence stem in the wild-type was observed in the form of a ring along the inner side of the outer wall of the inflorescence stem, and lignin involved in the formation of vascular bundles was observed in the form of projections extending outward from a point inside the inflorescence stem. As to the inflorescence stem slices of SALK_149993 and SALK_120377, lignin involved in the formation of vascular bundles was observed in the form of projections extending outward from an inside point as in the wild-type, but lignin involved in the formation of secondary walls (xylem) was observed in the form of a vague ring as compared with the wild-type. As to the NST1/NST3 gene disruption plant, lignin involved in the formation of vascular bundles was observed as in the wild-type, but lignin involved in the formation of secondary walls (xylem) was not observed.

Figure 3:
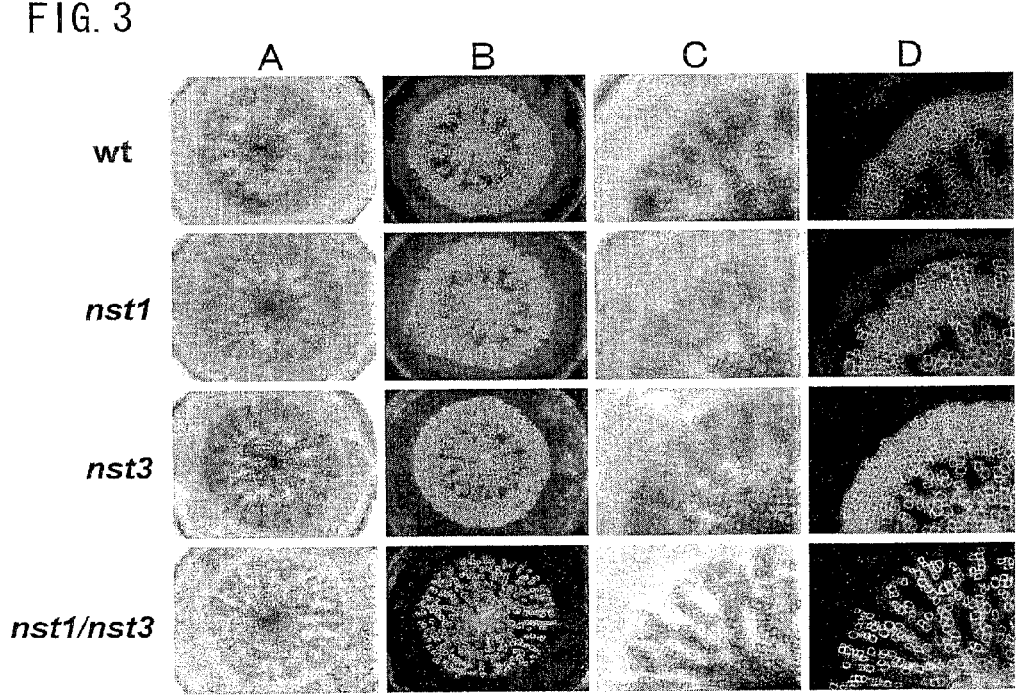
FIG. 3 is cross-sectional views of hypocotyls of the wild-type *Arabidopsis thaliana* and the mutant *Arabidopsis thaliana* in which NST1 gene and/or NST3 gene were disrupted, which hypocotyls were observed under a microscope.

FIG. 3 shows hypocotyl slices of the four plants, which slices were observed under a microscope (line A (low magnification) and line C (high magnification) and the same slices in which lignin was visualized (line B (low magnification) and line D (high magnification)).

Vascular bundles of the hypocotyls were observed in the form of lines extending in all directions, and secondary walls (xylem) of the hypocotyls were observed in the form of swaths overlapping the outer walls of the vascular bundles (lines A and C in FIG. 3). The area where lignin was synthesized was brighter than the other area and formed tiny bubbles (lines B and D in FIG. 3).

As shown in lines B and D in FIG. 3, as to the wild-type and SALK_149993, lignin involved in the formation of vascular bundles was observed in the form of lines extending in all directions, and lignin involved in the formation of secondary walls (xylem) was observed in the form of a swath overlapping the outer wall of the vascular bundle. As to the slice of SALK_120377, lignin involved in the formation of vascular bundle was observed as in the wild-type. However, lignin involved in the formation of a secondary wall (xylem) was observed in the form of a swath slightly narrower than that of the wild-type. Further, as to the NST1/NST3 gene disruption plant, lignin involved in the formation of vascular bundle was observed as in the wild-type, but lignin involved in the formation of secondary wall (xylem) was not observed.

As a result of the comparison between the plants in the degree of growth, no significant difference was found since they grew to a length of about 30 cm (the results are not shown).

Thus, it was found that in a case where the function of one of the transcription factor NST1 and the transcription factor NST3 was disrupted, the amount of lignin present in secondary walls (xylem) decreased or remains unchanged, whereas in a case where the functions of both the transcription factor NST1 and the transcription factor NST3 were disrupted, there existed almost no lignin in secondary walls (xylem).

Example 3

Effects of Transcription Factor NST1 or Transcription Factor NST3 on Natural Dehiscence of Pods As in Example 2, wild-type *Arabidopsis thaliana*, SALK_120377, SALK_149909, and NST1/NST3 gene disruption plant were grown, and these plants produced seeds. Respective pods of the plants were collected, and pod slices were prepared according to the following procedure.

Each of *Arabidopsis thaliana* pods was collected and then immersed and fixed in a FAA fixing solution (45% ethanol, 2.5% acetic acid, 2.5% formalin) for 12 hours. The fixed pod was immersed in (1) a mixture solution of 40% ethanol and 10% tertiary butyl alcohol, (2) a mixture solution of 50% ethanol and 20% tertiary butyl alcohol, (3) a mixture solution of 50% ethanol and 35% tertiary butyl alcohol, (4) a mixture solution of 45% ethanol and 55% tertiary butyl alcohol, and (5) a mixture solution of 25% ethanol and 75% butyl alcohol, in this order each for 30 minutes. After immersed in the mixture solution (5), the pod was immersed in 100% tertiary butyl alcohol twice each for more than 1 hour.

To 100% tertiary butyl alcohol in which the pod was immersed, an equal amount of paraffin, (heated at 60° C.) was added. This solution was let stand at 60° C. for 12 hours. After tertiary butyl alcohol was evaporated, the pod and paraffin were poured into a mold, and let stand at room temperature. As a result, paraffin became solid and the pod was embedded in paraffin. By using a microtome, successive pod slices were prepared to be 10 µm thick each.

The pod slices were floated on water dropped on slide glasses and then made adhere to the slide glasses by evaporating the water. The slide glasses to which the slices were adhered were dried on a hot plate at 38° C. The dried slide glasses were immersed in 100% xylene (twice each for 10 minutes). Paraffin dissolved therein was removed.

Figure 4A:
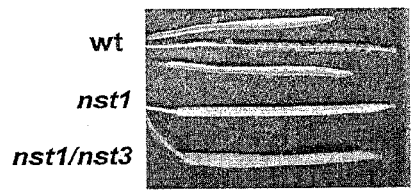
FIG. 4(*a*) is a view showing the wild-type *Arabidopsis thaliana* and the mutant *Arabidopsis thaliana* in which NST1 gene and/or NST3 gene were disrupted, which were observed under a microscope (low magnification).
Figure 4B:
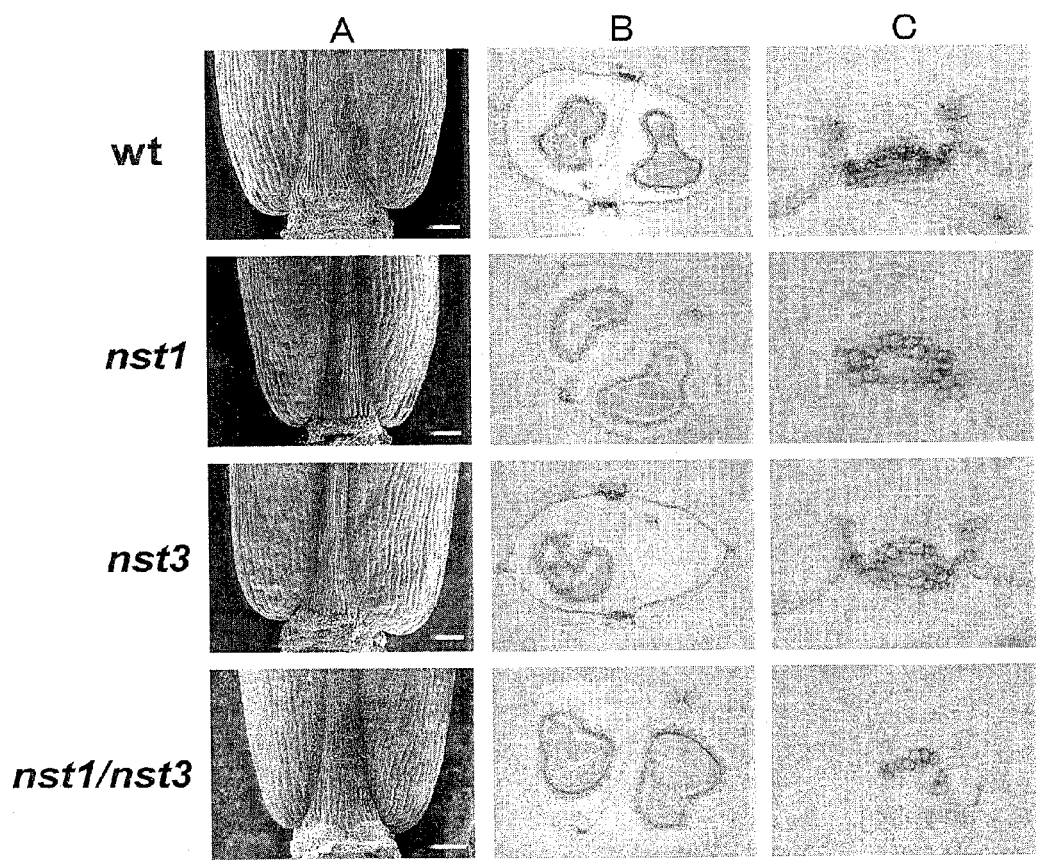

Next, each of the slide glasses from which paraffin was removed was immersed in (1) a mixture solution of 50% xylene and 50% ethanol for 1 minute, (2) 100% ethanol for 1 minute, (3) phloroglucinol solution of 95% ethanol for 2 minutes, and (4) 30% hydrochloric acid for 1 minute, in this order. After the immersion in the solution (4), the pod slice was filled with 15% hydrochloric acid, and the pod slice was observed in cross section under an optical microscope. FIGS. 4(a) and 4(b) show the results of observation of the pods and their slices of wild-type *Arabidopsis thaliana*, SALK_149993, SALK_149909, and NST1/NST3 gene disruption plant.

The pods of the wild-type *Arabidopsis thaliana* easily dehisced naturally, whereas fewer pods of the NST1 gene disruption plant dehisced naturally, as compared with the pods of the wild-type *Arabidopsis thaliana*. The pods of the NST1/NST3 gene disruption plant failed dehiscence at a higher frequency than the pods of the NST1 gene disruption plant (FIG. 4(a)).

FIG. 4(b) shows the sides of the roots (near stems) of the pods of the four plants (line A) and the slices into which the pods of the four plants were cut (line B (low magnification) and line C (high magnification), all of which were observed under a microscope.

In all of the photographs on line B, the pod was observed in such a form that two semicircles were combined, and these two semicircles were connected to each other via a region observed in the form of a small ellipse. In all of the photographs on line C, valve endodermal layer was observed inside the small ellipse in the pod, and a valve margin was observed at a region where the two semicircles and the small ellipse were in contact with each other and at a region near the contact region in the pod.

As shown on lines B and C in FIG. 4(b), as a result of observation of the pod slices of the wild-type plant, secondary wall thickenings were found in valve endodermal layer and a site called valve margin. Further, as a result of observation of the pod slices of the NST1 gene disruption plant, secondary wall thickenings were found in valve endodermal layer, but not in valve margin. Still further, as a result of observation of the pod slices of the NST1/NST3 gene disruption plant, almost no secondary wall thickenings were found in valve margin and valve endodermal layer.

From the above results, it was found that secondary wall thickenings were suppressed in the pod of the NST1 gene disruption plant. Further, as compared with the pod of the NST1 gene disruption plant, secondary wall thickenings were more strongly suppressed in the pod of the NST1/NST3 gene disruption plant.

In the course of drying of the pod, there is difference in contraction rate between a site where secondary wall thickenings occur and a site where no secondary wall thickenings occur. The difference in contraction rate is a tension required for the occurrence of natural dehiscence of pods. In proportion to the degree of suppression of secondary wall thickenings, natural dehiscence is inhibited in the pods of the NST1 gene disruption plant and the NST1/NST3 gene disruption plant.

Example 4

Measurement of Glucan and Lignin Contents

The wild-type *Arabidopsis thaliana* was grown as a control, and the NST1/NST3 gene disruption plant was grown as a plant in which the functions of the transcription factor NST1 and the transcription factor NST3 were disrupted. Cell wall component contents, glucan contents, and lignin contents of these two plants were measured and compared to each other. Each of the two plants was grown in five experiment sections. Table 2 shows mean value±standard deviation of measurement results in each of the experiment sections. In Table 2, each value of an objective substance (cell wall component, glucan, or lignin) is expressed in percentage by weight, in relative to the weight of the plant.

Quantitative measurements of the amounts of lignin and glucan in the cell wall components were carried out in the following procedure. Dried cell walls from which water-soluble and fat-soluble components were removed were used. An inflorescence stem of a mature *Arabidopsis thaliana* plant was cut by about 5 cm (directly measured weight is 250 to 350 mg) out of its proximal region, and then disrupted well in 50 mM sodium phosphate buffer (pH7). Subsequently, the inflorescence stem was immersed twice in 50% ethanol and four times in 100% ethanol (in each case, at 30° C. for 10 minutes) to remove water-soluble components therefrom. Next, the inflorescence stem was immersed twice in ethanol-toluene (1:1(v/v)) (at 60° C. for 10 minutes) to remove fat-soluble components therefrom. Cell wall residue that is insoluble was dried at 105° C. for 18 hours, and a dry weight thereof was then measured by weighing. After the obtained sample was hydrolyzed at 30° C. for 60 minutes with 0.3 mL of 72% (w/w) sulfuric acid, the thus hydrolyzed sample was diluted with 8.4 mL of distilled water (final concentration: 3% sulfuric acid) and then hydrolyzed at 121° C. for 60 minutes. After cooled at room temperature, the resulting sample was messed up to 10 mL with distilled water and mixed well, and thereafter 0.5 mL of the obtained supernatant was centrifuged for 5 minutes at 13,000×g. By using the supernatant, the amount of glucan-derived glucose liberated from the supernatant was measured by Glucose test kit Wako (Wako). Quantitative measurement of Klason lignin (acid-insoluble lignin) was carried out as follows: An insoluble precipitate obtained after acid hydrolysis was washed with distilled water for three times and dried at 105° C. for 18 hours. Subsequently, a dry weight of the insoluble precipitate was then measured by weighing.

TABLE 2

|  | Cell wall component content per direct weight | Cellulose content per direct weight | Cellulose content per dry weight | Lignin content per direct weight | Lignin content per dry weight |
|---|---|---|---|---|---|
| WT | 9.78 ± 2.35 | 3.25 ± 0.59 | 33.57 ± 2.38 | 1.66 ± 0.51 | 16.76 ± 1.66 |
| nst1/nst3 | 5.16 ± 0.33 | 1.73 ± 0.12 | 33.46 ± 1.13 | 0.41 ± 0.08 | 8.01 ± 1.48 |

All measurements in % by weight

FIG. 5 shows the values in Table 2 in graph form and the results of comparisons between the components contained in the wild-type and the NST1/NST3 gene disruption plant. FIG. 5(a) is a graph showing cell wall component contents per direct weight, FIG. 5(b) is a graph showing glucan contents per direct weight, FIG. 5(c) is a graph showing glucan contents per dry weight, FIG. 5(d) is a graph showing lignin contents per dry weight, and FIG. 5(e) is a graph showing lignin contents per dry weight. FIGS. 5(a) through (e) show the results of comparisons between the two plants. In Table 2 and FIG. 5, "direct weight" means a directly measured weight of a grown plant without subjected to any treatment prior to the measurement, and "dry weight" means a weight of the plant after dried.

A cell wall component content per direct weight of the wild-type plant was 9.78±2.35% by weight. A cell wall component content per direct weight of the NST1/NST3 gene disruption plant was 5.16±0.33% by weight. Glucan and lignin contents per direct weight of the wild-type plant were 3.25±0.59% by weight and 1.66±0.51% by weight, respectively. Glucan and lignin contents per direct weight of the NST1/NST3 gene disruption plant were 1.73±0.12% by weight and 0.41±0.08% by weight, respectively. Glucan and lignin contents per dry weight of the wild-type plant were 33.57±2.38% by weight and 16.76±1.66% by weight, respectively. Glucan and lignin contents per dry weight of the NST1/NST3 gene disruption plant were 33.46±1.13% by weight and 8.01±1.48% by weight, respectively (Table 2).

Figure 5A:
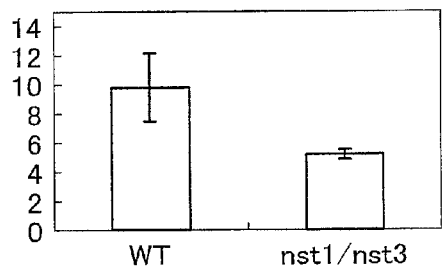
FIG. 5(*a*) is a view showing the result of comparison between the wild-type *Arabidopsis thaliana* and a NST1/NST3 gene disruption plant in terms of cell wall component content per direct weight.
Figure 5B:
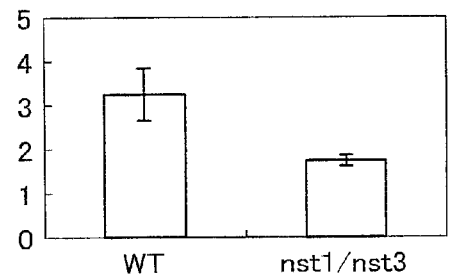
Figure 5C:
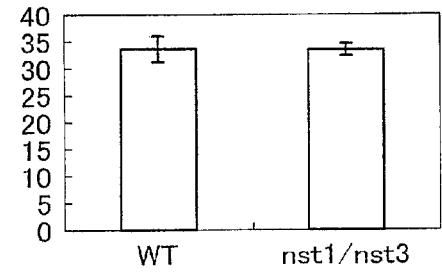
Figure 5D:
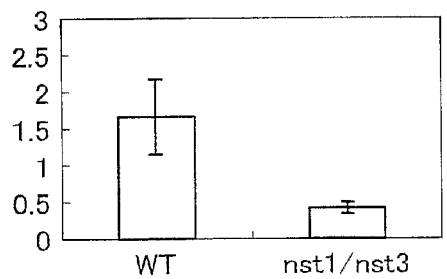
Figure 5E:
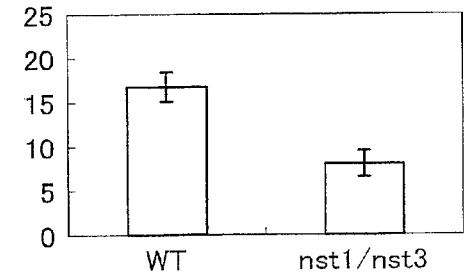

Regardless of whether the contents were measured per direct weight or dry weight, the lignin content of the NST1/NST3 gene disruption plant was less than half the lignin content of the wild-type plant (FIGS. 5(d) and 5(e)). The cell wall component content of the NST1/NST3 gene disruption plant was half that of the wild-type plant (FIG. 5(a)). The glucan content of the NST1/NST3 gene disruption plant was about half that of the wild-type plant (in the case where the glucan content was measured per direct weight) or almost the same as that of the wild-type plant (in the case where the glucan content was measured per dry weight) (Table 2, FIGS. 5(b) and 5(c)).

From the above results, it was revealed that the synthesis of lignin was suppressed in the NST1/NST3 gene disruption plant. Further, considering the results in Examples 2 and 3 together, it is suggested that natural dehiscence of pods is suppressed in the NST1/NST3 gene disruption plant due to suppression of the synthesis of lignin.

Example 5

Change Caused by Expression of NST1 Gene or NST3 Gene

Expression of the NST1 gene and/or the NST3 gene in thin slices of inflorescence stems or hypocotyls of *Arabidopsis thaliana* was analyzed by using a fusion gene in which a transcription control region and a GUS reporter gene in the NST1 gene or the NST3 gene were fused with each other.

First, to examine the promoter activities of the NST1 gene (At2g46770) and the NST3 gene (At1g32770), a promoter region of the NST1 gene was isolated by 2837 bp, and a promoter region of the NST3 gene was isolated by 3027 bp, and these promoter regions were ligated to upstream regions of the reporter genes GUS, respectively, to construct chimeric genes. With these chimeric genes, *Arabidopsis thaliana* was transformed by Floral dip method.

Inflorescence stems or hypocotyls of the obtained transformant were embedded in 3% agar. 100 μm-thick slices made by a vibrating microtome (HM-650V) were observed under optical microscope. Further, the same slices were observed under ultraviolet radiation to observe autofluorescence emitted by lignin that constitutes secondary walls (xylem) (A through J in FIG. 6).

Also, it was confirmed that overexpression of the NST3 gene induced ectopic formation of secondary walls (xylem). In order to overexpress the NST3 gene, a fusion gene in which a NST3 protein coding region was ligated to a CaMV35S promoter was prepared. With this fusion gene, *Arabidopsis thaliana* was transformed by a conventional method (Floral dip method).

Figure 6:
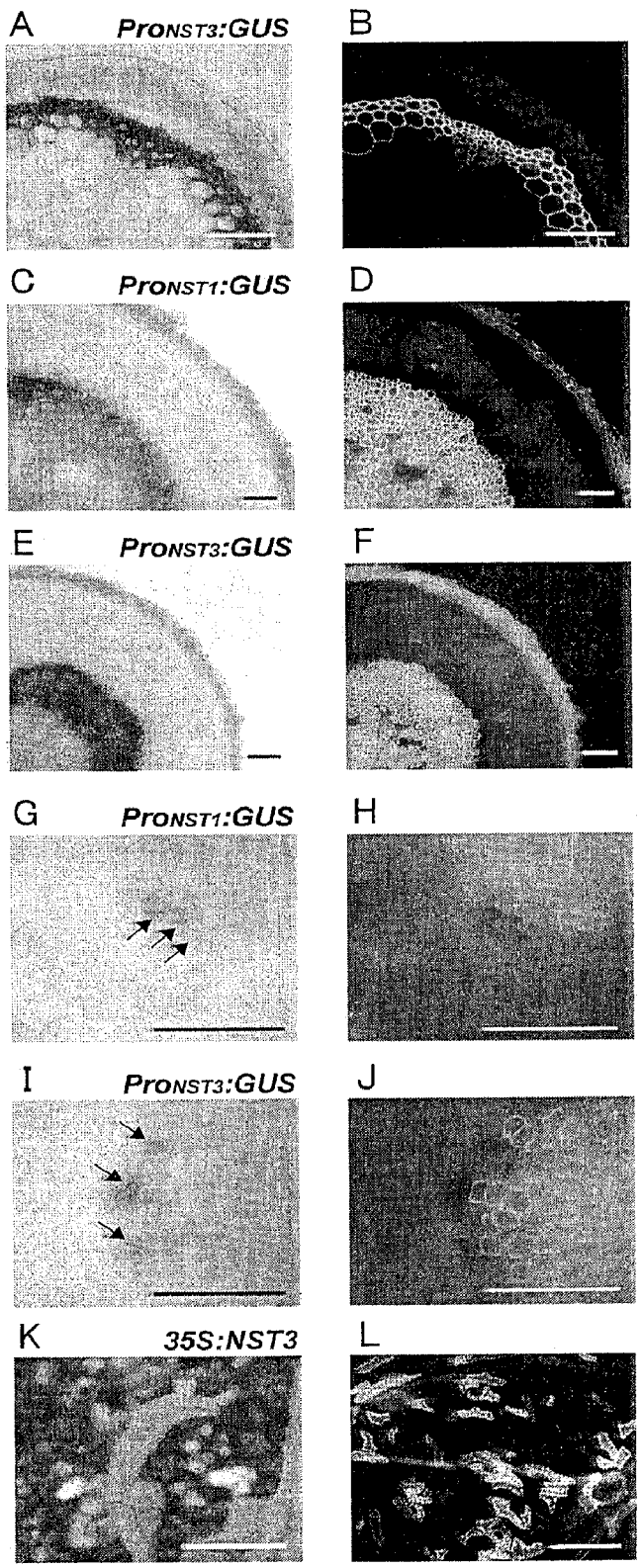
FIG. 6 is a view showing the sites where NST1 gene or NST3 gene is possibly expressed and showing that overexpression of NST3 gene in a plant induces ectopic formation of xylem.

Rosette leaves of the obtained transformant were immersed in 70% lactic acid at 50° C. for 12 hours and observed under ultraviolet radiation to confirm autofluorescence emitted by lignin that constitutes secondary walls (xylem) (K and L in FIG. 6).

FIG. 6 shows that the NST3 gene has promoter activities at sites where xylems are formed as in the case of the NST1 gene, and shows that overexpression of the NST3 gene in a plant induces ectopic formation of xylems. FIG. 6 shows inflorescence stems (A and B), hypocotyls (C through F), immature hypocotyls (G through J), and leaves (K and L). In the sections shown on the left side of FIG. 6, fluorescence is emitted at sites where xylems are formed. The sections (B, D, F, H, J, and L) shown on the right side are the same as the sections (A, C, E, G, I, and K) shown on the left side, except that they were observed under ultraviolet radiation.

A: In inflorescence stem, sites having promoter activities of the NST3 gene (sites where xylems are formed) are stained.

C and E: In hypocotyl, sites having promoter activities of the NST1 gene (C) or the NST3 gene (E) (sites where xylems are formed) are stained.

G and I: In immature hypocotyl, sites having promoter activities of the NST1 gene (G) or the NST3 gene (I) (cells differentiating into vascular vessels) are stained (indicated by arrows in G and I in FIG. 6).

K: Overexpression of the NST3 gene causes a change such as upward curling of a leaf. When such a leaf is observed under ultraviolet radiation, ectopic formation of xylems can be confirmed (L).

Example 6

Suppression of Formation of Xylems Due to NST1/NST3 Double Gene Disruption

Double gene disruption lines of the NST1 gene and the NST3 gene were constructed as follows: Gene disruption lines of the NST1 gene and the NST3 gene (SALK__120377, SALK__149993, SALK__149909, and SALK__131657) were obtained from *Arabidopsis* Biological Resource Center (ABRC, Ohio, U.S.A.). To construct double gene disruption lines of both the NST1 gene and the NST3 gene, SALK__120377 and SALK__149909 (nst1-1 and nst3-1) are crossed, and SALK__149993 and SALK__131657 (nst1-2 and nst3-2) are crossed to obtain respective seeds in the next generation.

To conform that no transcripts of interest are caused by gene disruption in the double gene disruption lines of the NST1 gene and the NST3 gene, all RNAs were extracted from the inflorescence stems of the wild-type line and the double gene disruption line by using RNeasy plant kit, and the presence or absence of transcripts of interest corresponding to the full-length NST1 gene and the full-length NST3 gene was examined by RT-PCR. A transcript of the TUB gene was used as a positive control.

Figure 7A:
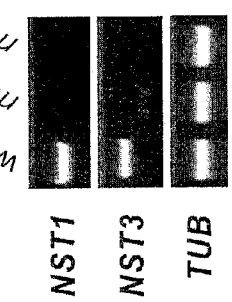
FIG. 7(*a*) is a diagram of gene disruption lines of NST1 gene and NST3 gene and a view showing the positions where tags are inserted in each of the gene disruption line.
Figure 7B:
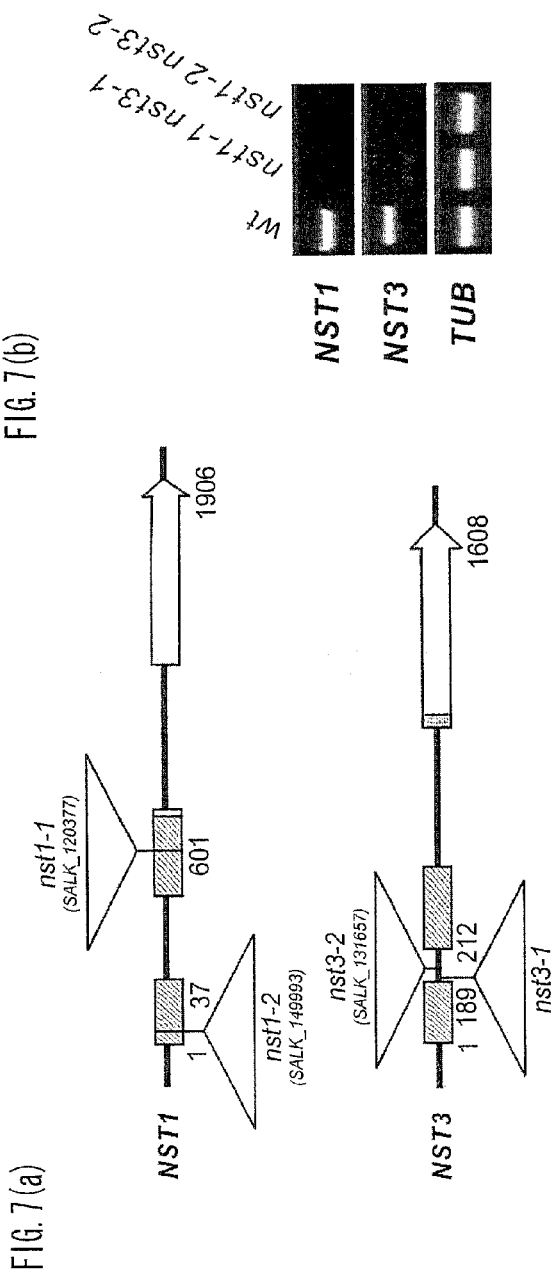

FIG. 7(a) is a diagram of gene disruption lines of the NST1 gene and the NST3 gene and a diagram showing the positions where tags are inserted in the gene disruption lines. FIG. 7(b) shows the result of analysis of the disruption lines and shows that neither NST1 gene nor the NST3 gene are expressed in the double gene disruption lines.

To examine the formation of xylems in the double gene disruption line, 100 μm-thick slices of inflorescence stems or hypocotyls were prepared and observed under optical microscope, as in Example 5. Further, the same slices were observed under ultraviolet radiation to confirm autofluorescence emitted by lignin that constitutes secondary walls (xylem).

For more specific observation of the state of secondary walls, each of the inflorescence stems was fixed in a buffer solution containing 2% paraformaldehyde and 2% glutaraldehyde and a buffer solution containing 2% osmium tetroxide and then embedded in Q651 resin, and 80 to 90 nm-thick slices were prepared. The slices were stained with uranyl acetate and lead citrate and observed by a JEM1200EX transmission electron microscope.

Figure 7C:
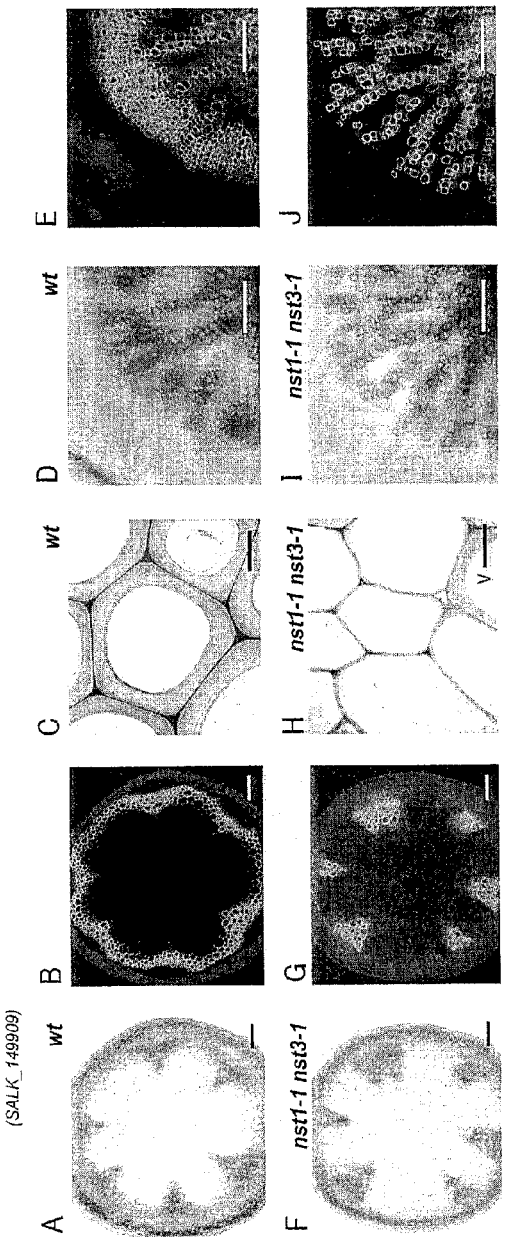

A through J in FIG. 7(c) show that the formation of xylems is significantly suppressed in inflorescence stems and hypocotyls of the NST1/NST3 double gene disruption line. A is a view showing the state of the slice of inflorescence stem of the wild-type line when observed under transmitted light radiation. B is a view showing the state of the slice of inflorescence stem of the wild-type line when observed under ultraviolet radiation. F is a view showing the state of the slice of inflorescence stem of the NST1/NST3 double gene disruption line when observed under transmitted light radiation. G is a view showing the state of the slice of inflorescence stem of the NST1/NST3 double gene disruption line when observed under ultraviolet radiation. From A, B, and F, it is apparent that in the double gene disruption lines, the formation of xylems is completely suppressed, except in vascular vessels. C is a view showing the state of cells for fibers of inflorescence stems of the wild-type line when observed under transmission electron microscope. H is a view showing the state of cells for fibers of inflorescence stems of the NST1/NST3 double gene disruption line when observed under transmission electron microscope. From C and H, it is apparent that in the double gene disruption lines secondary cell walls are completely lost except in vascular vessels (indicated by v in H of FIG. 7(c)). D is a view showing the state of the slice of hypocotyl of the wild-type line when observed under transmitted light radiation. E is a view showing the state of the slice of hypocotyl of the wild-type line when observed under ultraviolet radiation. I is a view showing the state of the slice of hypocotyl of the NST1/NST3 double gene disruption line when observed under transmitted light radiation. J is a view showing the state of the slice of hypocotyl of the NST1/NST3 double gene disruption line when observed under ultraviolet radiation. From D, E, I, and J, it is apparent that in the double gene disruption lines the formation of xylems is completely suppressed except in vascular vessels.

Example 7

Strength of Stems of NST1/NST3 Double Gene Disruption Lines

Figure 8A:
FIG. 8(*a*) is a view showing inflorescence stems of the wild-type line and the NST1/NST3 double gene disruption line both grown under short-day conditions.
Figure 8B:
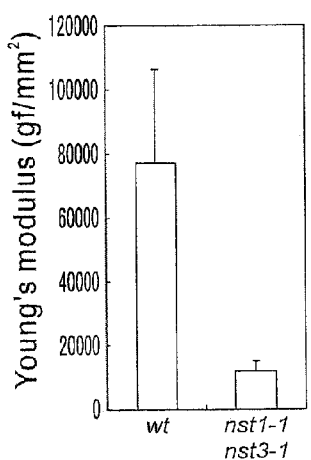

As a result of comparison between inflorescence stems of the wild-type *Arabidopsis thaliana* line and the NST1/NST3 double gene disruption line both grown under short-day conditions (FIG. 8(a)), the wild-type line remains upright (left side) since the strength of inflorescence stem grown under short-day conditions is higher than the strength of inflorescence stem grown under long-day conditions. However, inflorescence stem of the NST1/NST3 double gene disruption line is no longer able to remain upright (right side) since lignin is not accumulated in secondary walls in the NST1/NST3 double gene disruption line. In view of this, growth rates of the inflorescence stems were measured, and Young's moduli (strengths of stems) were calculated (FIG. 8(b)). This revealed that Young's modulus of the inflorescence stem of the NST1/NST3 double gene disruption line was lower than that of inflorescence stem of the wild-type line, and stem tissues of the NST1/NST3 double gene disruption line were lower in strength and easily broken. This results from suppression of lignin accumulation in the inflorescence stem of the NST1/NST3 double gene disruption line.

Figure 8C:
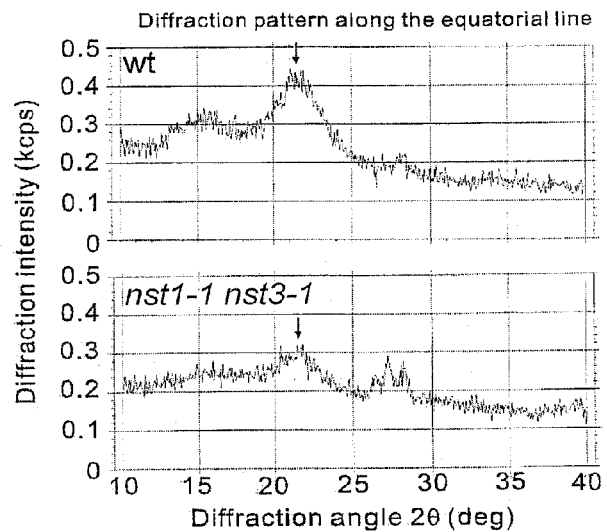
Figure 8D:
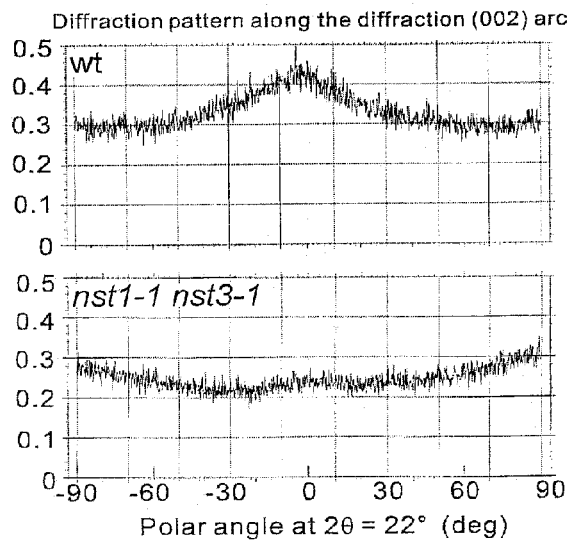

Next, to examine the crystal state of cellulose microfibrils that constitute secondary walls (xylem), crystal diffraction of dried inflorescence stems was analyzed by using x-ray diffraction analyzing device. The analysis was carried out under Nickel-filtered Cu Ka radiation (wavelength, 0.154 nm) at 30 kV and 35 mA. FIGS. 8(c) and 8(d) show the results of x-ray diffraction analysis of the crystallization of cellulose microfibrils that constitute secondary cell walls in inflorescence stems of the wild-type line and the NST1/NST3 double gene disruption line. FIGS. 8(c) and 8(d) show the results of analysis of the same samples in different two directions. Specifically, FIG. 8(d) shows distribution of diffraction intensities in another dimension at diffraction angle (2θ=22°), which corresponds to diffraction peaks in FIG. 8(c) (indicated by arrows in FIG. 8(c)). In the wild-type line, a diffraction peak corresponding to cellulose microfibrils is clearly distinctive, but nearly indistinctive in the double gene disruption line. Thus, cellulose content significantly decreases in the NST1/NST3 double gene disruption line.

As shown in Example 4, lignin content of the NST1/NST3 gene disruption line is lower by 50% than that of the wild-type line, but there is no significant difference in glucan content per dry weight between both of the lines (FIGS. 5(c) and 5(e) and Table 2). Considering this fact and the results of x-ray crystal diffraction together, it is apparent that glucan, a constituent component of cellulose, is accumulated without being crystallized.

Example 8

Change of Gene Expression in NST1/NST3 Double Gene Disruption Line

To examine the expression of a gene that encodes an enzyme involved in synthesis of lignin and a gene that encodes an enzyme involved in synthesis of cellulose, promoter regions of lignin synthesis-related gene IRX3 and cellulose synthesis-related gene CAD-D (1137 bp and 1146 bp, respectively) were ligated to upstream regions of reporter genes GUS, respectively, to construct reporter genes. With these reporter genes, the wild-type *Arabidopsis thaliana* line and the NST1/NST3 double gene disruption line were transformed by Floral dip method. After inflorescence stem of each of the obtained transformants was embedded in 3% agar, 100 μm-thick slices made by a vibrating microtome (HM-650V) were observed under optical microscope. Further, the same slices were observed under ultraviolet radiation to confirm autofluorescence emitted by lignin that constitutes secondary walls (xylem).

Figure 9A:
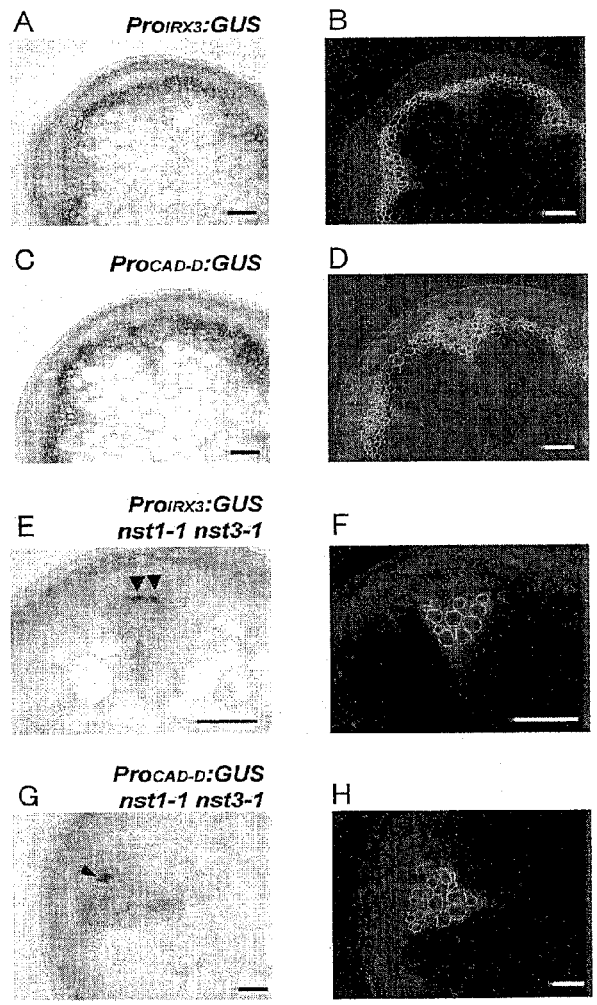
FIG. 9(*a*) is a view showing that expressions of genes that encode enzymes involved in synthesis of lignin and cellulose, which are main components of xylem, are suppressed in the double gene disruption line of the NST1 gene and the NST3 gene.
Figure 9B:
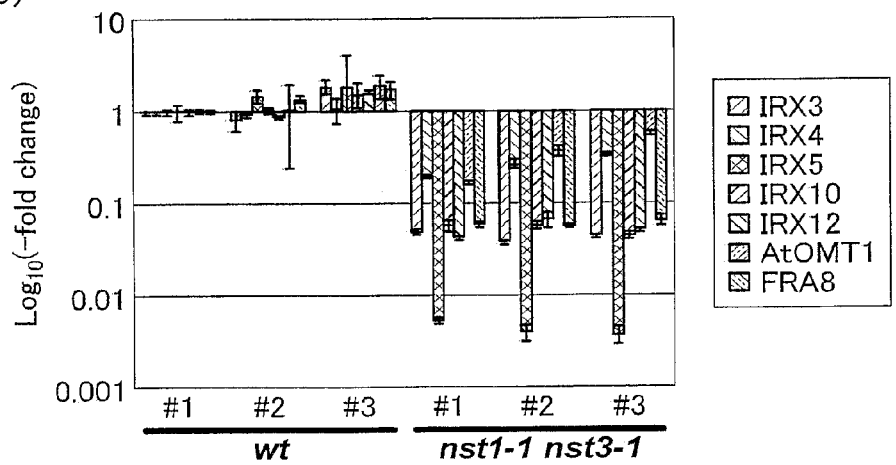

A through H in FIG. 9(*a*) show that expressions of genes that encode enzymes involved in synthesis of lignin and cellulose, which are main components of xylem, are suppressed in the double gene disruption line of the NST1 gene and the NST3 gene. A is a view showing promoter activity of the IRX3 gene in inflorescence stem of the wild-type line. B is a view showing the state of inflorescence stem of the wild-type line when observed under ultraviolet irradiation. C is a view showing promoter activity of the CAD-D gene in inflorescence stem of the wild-type line. D is a view showing the state of inflorescence stem of the wild-type line when observed under ultraviolet irradiation. In A and C, sites having the promoter activities are stained. E is a view showing promoter activities of the IRX3 gene in inflorescence stem of the NST1/NST3 double gene disruption line. F is a view showing the state of inflorescence stem of the NST1/NST3 double gene disruption line when observed under ultraviolet irradiation. G is a view showing promoter activities of the CAD-D gene in inflorescence stem of the NST1/NST3 double gene disruption line. H is a view showing the state of inflorescence stem of the NST1/NST3 double gene disruption line when observed under ultraviolet irradiation. In E and G, sites having the promoter activities are stained.

It was further examined in gene expression level that expressions of the genes that encode enzymes involved in synthesis of lignin and cellulose, which are main components of xylem, were suppressed in the double gene disruption line of the NST1 gene and NST3 gene. Expressions of genes that encode enzymes involved in synthesis of components constituting secondary walls, such as lignin and cellulose, were quantified by cyber green method using real time RCR system ABI-7300. Relative expression value when an average expression value of Individual No. 1 of the wild-type line was calculated. FIG. 9(*b*) is a graph showing comparison between the wild-type line and the double gene disruption line in expressions of the genes that encode enzymes involved in synthesis of secondary walls. The degree of expression of the genes that encode the enzymes in the double gene disruption line was much lower than the degree of expression of the genes that encode the enzymes in the wild-type line.

Example 9

Inhibition of Function of NST1 Gene or NST3 Gene by Transcription Repressor Chimeric repressor expressing plant for NST1 or NST3 was produced according to the following procedure: To suppress the formation of xylems, DNA encoding transcription repression peptide (SRDX) was ligated in-frame to the 3' end of the NST1 gene or the NST3 gene, so as to construct a chimeric gene that is located below a promoter of the NST1 gene or the NST3 gene (by using chimeric repressor for NST1 or NST3). Note that chimeric repressor genes were constructed respectively consisting of the following three kinds of combinations:

1) NST1 gene promoter, NST1 coding region, and SRDX (D and E in drawing);
2) NST3 gene promoter, NST3 coding region, and SRDX (F and G in drawing); and
3) NST3 gene promoter, NST1 coding region, and SRDX (H and I in drawing).

With these chimeric repressors, *Arabidopsis thaliana* was transformed by Floral dip method. Inflorescence stem of each of the obtained transformants was embedded in 3% agar. Thereafter, 100 μm-thick slices made by a vibrating microtome (HM-650V) were observed under optical microscope. Further, the same slices were observed under ultraviolet radiation to observe autofluorescence emitted by lignin that constitutes secondary walls (xylem).

Figure 10:
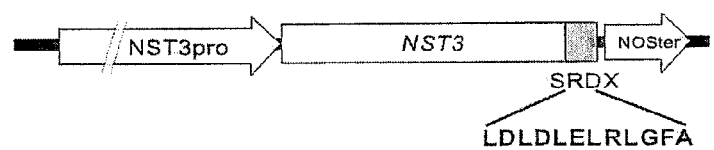
FIG. 10(*a*) is a typical example of constructs of chimeric DNA that encodes a chimeric protein.
Figure 10:
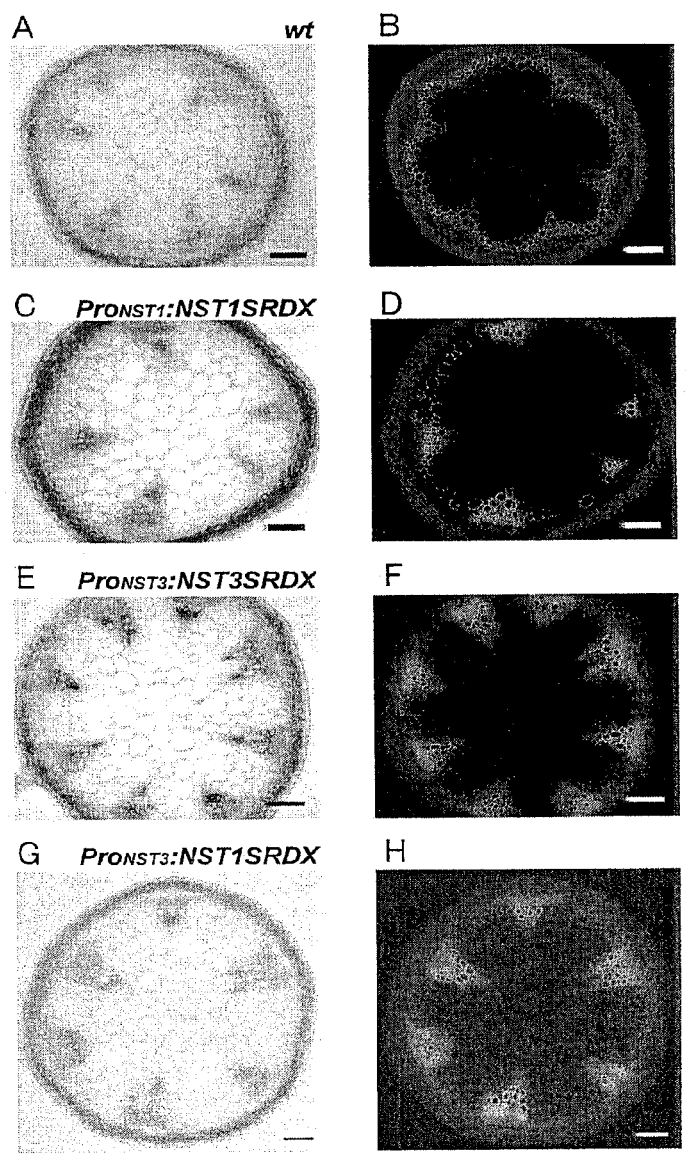

FIG. 10 shows that the NST1 chimeric repressor or the NST3 chimeric repressor can effectively suppress the formation of xylems, as in the case of the double gene disruption line of the NST1 gene and the NST3 gene. FIG. 10(*a*) shows a typical example of constructs of chimeric DNA that encodes a chimeric protein. In FIG. 10(*b*), A shows inflorescence stem of the wild-type line when observed under transmitted light radiation, B shows inflorescence stem of the wild-type line when observed under ultraviolet irradiation, C shows inflorescence stem of ProNST1:NST1SRDX expression line when observed under transmitted light radiation, D shows inflorescence stem of ProNST1:NST1SRDX expression line when observed under ultraviolet irradiation, E shows inflorescence stem ProNST3:NST3SRDX expression line when observed under transmitted light radiation, F shows inflorescence stem of ProNST3:NST3SRDX expression line when observed under ultraviolet radiation, G shows inflorescence stem of ProNST3:NST1SRDX expression line when observed under transmitted light radiation, and H shows inflorescence stem of ProNST3:NST1SRDX expression line when observed under ultraviolet radiation. It is apparent that the formation of xylems is overwhelmingly suppressed in the ProNST3:NST3SRDX expression line (E and F) and the ProNST3:NST1SRDX expression line (G and H). Thus, with the use of a chimeric protein according to the present invention, it is possible to effectively suppress the generation of cellulose and lignin in woody plants. As described previously, the use of a chimeric protein according to the present invention can induce the accumulation of glucan, which is non-crystallized cellulose. This makes it possible to produce a plant suitable for production of bioethanol.

The features of a plant in which both the NST1 gene and the NST3 gene are doubly disrupted are observed in a plant in which either a chimeric protein for NST1 or a chimeric protein for NST3 is expressed, not in a plant in which only the NST1 gene is disrupted and a plant in which only the NST3 gene is disrupted. This shows that the technique using a chimeric protein as a transcription repressor is infinitely superior to the gene disruption technique.

Example 10

Reduction of Lignin and Crystalline Cellulose due to Inhibition of Function of NST1 Gene or NST3

A method of producing ethanol from biomass mainly has the following two steps: saccharification step (step of extracting a monosaccharide such as glucose from a polysaccharide such as glucan); and fermentation step (step of converting extracted monosaccharide into ethanol with the activity of yeast or the like). The saccharification step out of the two steps includes enzymic treatment (cellulase treatment) and physical and chemical treatment (acid hydrolysis, hot-compressed water treatment etc.), which are the rate-determining steps of a reaction. For reduction of production cost and environmental load, it is important to simplify the saccharification step.

Woody biomass (lignocellulose), which is the most carbon-neutral biomass on earth, has received attention as a material for use in ethanol production. However, it is extremely difficult to decompose lignin-binding cellulose, which is chemically more stable than cellulose alone. This prevents industrial applications of cellulose. As such, there has been demand for woody biomass which realizes easier saccharification.

In a plant (nst1/nst3 double mutant plant) in which the functions of two transcription factors (NST1 and NST3) of *Arabidopsis thaliana* which factors control biosynthesis of xylem are suppressed or a plant which expresses a NST1 chimeric repressor (or NST3 chimeric repressor) that dominantly regulates downstream of a NST transcription factor (In the present examples, such a plant will be referred to as NST chimeric repressor expressing plant), the synthesis of secondary walls is suppressed and reductions of crystalline cellulose and lignin are observed. In these plants, Young's modulus of inflorescence stem is low and their fibers are easily broken.

As a result of examining a total amount of glucan in a given dried cell wall component of the plant in which the function of NST transcription factor was suppressed or of the NST chimeric repressor expressing plant, the total amount of glucan was the same as a total amount of glucan in the wild-type line. From this result, it is considered that non-crystalline cellulose (glucan) is accumulated in the plant in which the NST transcription factor is suppressed or the NST chimeric repressor expressing plant. Non-crystalline cellulose itself is more susceptible to enzymic treatment and physical and chemical treatment (more likely to be saccharified) than crystalline cellulose. Also, it is considered that non-accumulation of lignin facilitates enzymic treatment and physical and chemical treatment (which are major factors responsible for the promotion of saccharification).

Thus, it was assumed that the cell wall component of the plant in which the function of NST transcription factor was suppressed or the NST chimeric repressor expressing plant was more likely to be saccharified. In view of this, to compare saccharification rates of the wild-type line, nst double mutant plant, and the NST chimeric repressor expressing plant, glucan in the cell wall component in each plant was subjected to saccharification by using a commercially available cellulase.

As in the quantification of the cell wall component, a dried cell wall component was extracted from a plant tissue (inflorescence stem). Two strains were prepared as samples from each of the wild-type line, the nst double mutant plant, and the NST chimeric repressor plant, and three individuals were sampled from each of the prepared strains.

About 2 mg of dried cell wall component of each plant was placed in 1.5 ml Eppendorf tube, and measured by weighing. To the dried cell wall component was added 1000 µl of commercially available enzyme (cellulase) solution (1% Celluclast 1.5 L (derived from *Trichoderma reesei*), 0.2% Novozyme 188 (derived from *Aspergillus niger*), 0.05 M Citrate-Na buffer (pH4.8), and titer of 400FPU/g-substrate) that had been filtered in advance. The mixture solution was incubated in a thermostat bath at 50° C. while shaken to obtain enzymatic reaction in a homogeneous system. 0 hour, 0.5 hour, 1 hour, 2 hours, and 4 hours after initiation of the reaction, 10 µl of solution was sampled from each reaction system.

Immediately after the sampling, the sampled solution was allowed to stand on a block incubator at 100° C. for 5 minutes to inactivate the enzyme, and then cooled on ice for 1 minute. Subsequently, the resulting solution was centrifuged at 10,000 rpm for 10 minutes. In 5 µl of supernatant, glucose generated from β-1,4-glucan (crystalline cellulose and non-crystalline cellulose) in the cell wall component was quantified by using Glucose C-II Test WAKO (WAKO).

Out of a total amount of glucan in each cell wall component that had been quantified in advance, a proportion of weight of glucan generated by cellulase treatment (0.9 times the weight of glucose) was expressed in scarification rate (scarification rate (% by weight))=(weight of glucose×0.9/total weight of glucan)×100).

Figure 11:
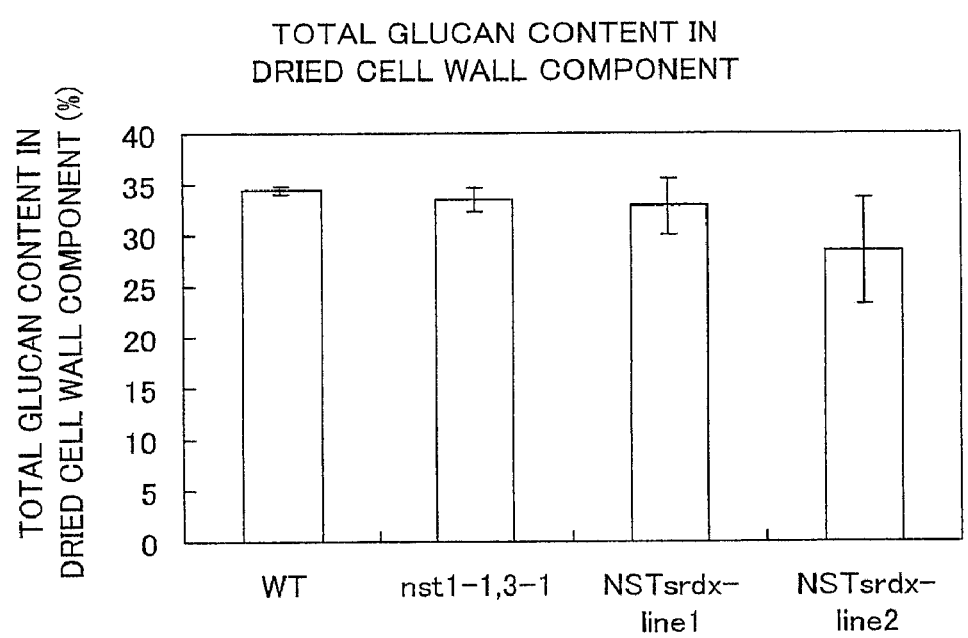
FIG. 11 is a view showing the result of comparison of the amounts of glucan in the dried cell wall components of the wild-type line, the nst double mutant plant, and the NST chimeric repressor plant.

FIG. 11 shows comparison of the amounts of glucan in the dried cell wall components. It is apparent that in all of the strains, glucan (derived from crystalline cellulose and non-crystalline cellulose) makes up 30 to 35% of the dried cell wall component, and there is no difference in the amount of glucan between the wild-type line, the nst double mutant plant, and the NST chimeric repressor expressing plant.

Figure 12:
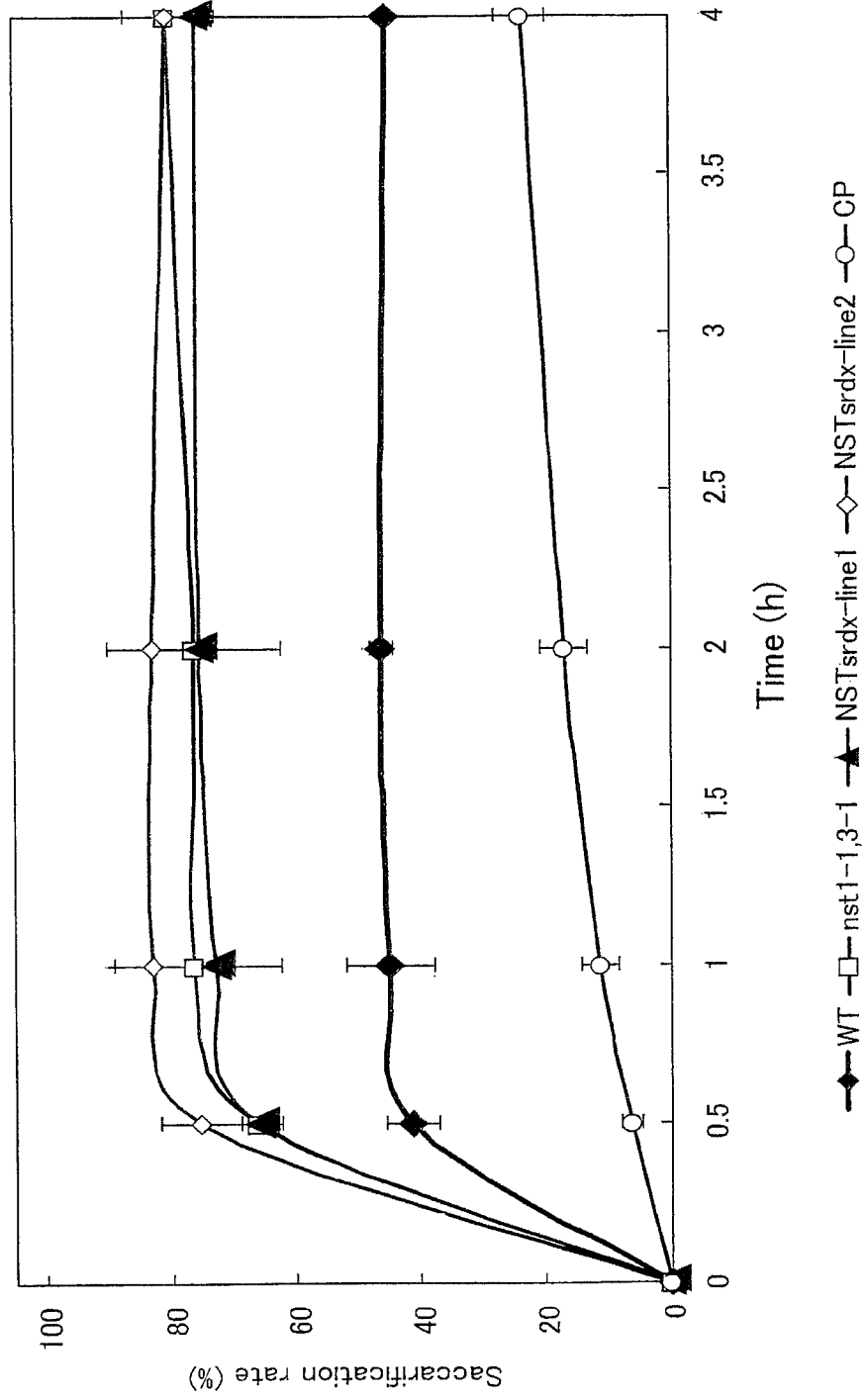
FIG. 12 is comparison of time-course changes in saccharification rate of a total amount of glucan contained in the dried cell walls of the wild-type line, the nst double mutant plant, and the NST chimeric repressor plant.
Figure 13:
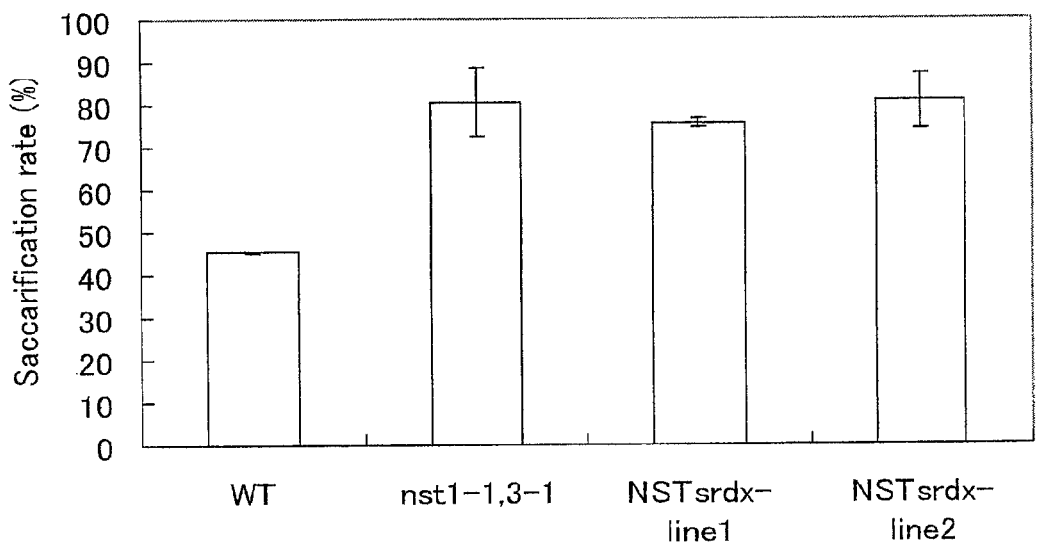
FIG. 13 is a view showing saccharification rates (4 hours after initiation of cellulase treatment) in a total amount of glucan contained in the dried cell walls of the wild-type line, the nst double mutant plant, and the NST chimeric repressor plant.

FIG. 12 shows comparison of changes over time in saccharification rate of a total amount of glucan contained in the dried cell walls, due to cellulase treatment. FIG. 13 shows saccharification rates 4 hours after initiation of the reaction. It is apparent that all of the strains reached a plateau about 1 hour after initiation of the reaction. However, the wild-type line reached a plateau at approximately 45% of saccharification rate, whereas the nst double mutant plant and the NST chimeric repressor plant reached a plateau at approximately 80% of saccharification rate. This result revealed that the nst double mutant plant and the NST chimeric repressor expressing plant had glucan more likely to be saccharified than the wild-type line, and a large part of glucan contained as the cell wall component was saccharified. A low saccharification rate of the wild-type line is considered to result from inhibited enzyme reaction caused by crystallization of glucan (crystalline cellulose) and binding of accumulated lignin to cellulose. On the other hand, in the nst double mutant plant and the NST chimeric repressor plant, it is considered that the enzyme reaction easily proceeds due to nonexistence of accumulated lignin and exposure of non-crystalline cellulose, with the result that a high saccharification rate is obtained.

CP in FIG. 12 represents fine particles of crystalline cellulose (cellulose powder manufactured by Whatman) and used as a barometer of enzyme activity. CP gradually underwent saccharification even after the cell wall sample reached a plateau. This shows that there occurs no inactivation of the enzyme used for the reaction system in the present experiment (i.e. the enzyme remained activated), which shows that the cell wall sample reached a plateau because saccharification reaction reached a plateau.

These experiments revealed that the plants in which the function of the NST transcription factor was suppressed (nst double mutant plant and NST chimeric repressor plant) produced glucan that easily underwent saccharification without changing the amount of glucan in the cell wall component. This result shows that effective use of the NST chimeric repressor makes it possible to artificially change the quality of lignocellulose in woody biomass and thus to produce biomass that is effective for bioethanol production.

In order to solve the above problem, a producing method of a plant according to the present invention in which the amounts of lignin and cellulose are reduced without reducing the amount of glucan, includes the step of inhibiting the function of a particular transcription factor (polypeptide having the amino acid sequence represented by SEQ ID NO: 74) in a plant. This makes it possible to produce a plant in which the amounts of lignin and cellulose are reduced without reducing the amount of glucan. Therefore, a producing method of the plant is not limited as long as it can inhibit the function of the polypeptide.

Further, in order to solve the above problem, a producing method of a plant according to the present invention in which natural dehiscence of pods is suppressed, includes the step of inhibiting the function of a particular transcription factor (polypeptide having the amino acid sequence represented by SEQ ID NO: 74) in a plant. This makes it possible to produce a plant in which natural dehiscence of pods is suppressed. Therefore, a producing method of the plant is not limited as long as it can inhibit the function of the polypeptide.

Specific embodiments or examples implemented in BEST MODE FOR CARRYING OUT THE INVENTION only show technical features of the present invention and are not intended to limit the scope of the invention. Variations can be effected within the spirit of the present invention and the scope of the following claims.

INDUSTRIAL APPLICABILITY

In the present invention, by inhibiting the function of a transcription factor that promotes transcription of a gene associated with the amount of lignin and the amount of cellulose, it is possible to obtain a plant in which the amounts of lignin and cellulose are reduced without reducing the amount of glucan. The obtained glucan is in the state of being highly easily undergoing saccharification. Lignocellulose is the best biomass on earth and expected as a material for next-generation biofuel whose environmental load is low. The present invention can be a new approach for artificially producing lignocellulose that easily undergoes saccharification and is suitable for ethanol production. As such, the present invention can be means for solving energy problems with human beings have been faced, and industrial applicability of the present invention is immeasurable. Further, in the obtained plant, natural dehiscence of pods is suppressed. Thus, the present invention is highly useful since it is applicable to agriculture, forestry, agribusiness, processing industries for agricultural products, and food industries, and further it can make a significant contribution to oil manufacturing industries.

The invention claimed is:

1. A method of reducing amounts of lignin and cellulose of a plant without reducing an amount of glucan in the plant, comprising the steps of:
   inhibiting a function of a polypeptide having the amino acid sequence set forth in SEQ ID NO: 74 in the plant; and
   measuring the amount of glucan in the plant cell wall, wherein the amount of glucan is not reduced relative to a non-transformed plant;
   wherein the step of inhibiting the function is carried out by causing the plant to produce a fusion protein in which the polypeptide having the amino acid sequence set forth in SEQ ID NO:74 is fused with a functional peptide capable of converting an arbitrary transcription factor into a transcription repressor.

2. The method according to claim 1, wherein the functional peptide has an amino acid sequence set forth in any one of SEQ ID NO: 1 through 17.

3. The method according to claim 1, wherein
   the plant includes at least one of: an adult plant; a plant cell; a plant tissue; a callus; and a seed.

* * * * *

```
SEQUENCE LISTING

<160> NUMBER OF SEQ ID NOS: 179

<210> SEQ ID NO 1
<211> LENGTH: 12
<212> TYPE: PRT
<213> ORGANISM: Nicotiana tabacum

<400> SEQUENCE: 1

Asp Leu Asp Leu Asn Leu Ala Pro Pro Met Glu Phe
 1               5                  10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence:Artificially
      Synthesized Amino Acid  Sequence

<400> SEQUENCE: 2

Leu Asp Leu Asn Leu Ala Pro Pro Met Glu Phe
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 3

Leu Asp Leu Asn Leu Ala Ala Ala Ala Ala Ala
 1               5                  10

<210> SEQ ID NO 4
<211> LENGTH: 10
<212> TYPE: PRT
<213> ORGANISM: Arabidopsis thaliana
```

```
<400> SEQUENCE: 4

Leu Asp Leu Glu Leu Arg Leu Gly Phe Ala
 1               5                  10

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 5

Asp Leu Glu Leu Arg Leu
 1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 6

Leu Asp Leu Gln Leu Arg Leu Gly Tyr Tyr
 1               5                  10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 7

Leu Asp Leu Glu Leu Arg Leu
 1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 8

Leu Asp Leu Glu Leu Ala Ala Ala Ala Ala Ala
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 9

Leu Asp Leu Glu Leu Arg Leu Ala Ala Ala
 1               5                  10

<210> SEQ ID NO 10
<211> LENGTH: 8
<212> TYPE: PRT
<213> ORGANISM: Artificial Sequence
```

```
<220> FEATURE:
<223> OTHER INFORMATION: Description of Artificial Sequence:Artificially
      Synthesized Amino Acid Sequence

<400> SEQUENCE: 10

Leu Asp Leu Glu Leu Arg Leu Gly
  1               5

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 11

Phe Asp Leu Asn Phe Ala Pro Leu Asp Cys Val
  1               5                  10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 12

Phe Asp Leu Asn Ile Pro Pro Ile Pro Glu Phe
  1               5                  10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 13

Phe Gln Phe Asp Leu Asn Phe Pro Pro Leu Asp Cys Val
  1               5                  10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 14

Asp Leu Asp Leu Arg Leu
  1               5

<210> SEQ ID NO 15
<211> LENGTH: 35
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 15

Val Gly Pro Thr Val Ser Asp Ser Ser Ser Ala Val Glu Glu Asn Gln
  1               5                  10                  15

Tyr Asp Gly Lys Arg Gly Ile Asp Leu Asp Leu Asn Leu Ala Pro Pro
```

```
                    20                  25                  30

Met Glu Phe
        35

<210> SEQ ID NO 16
<211> LENGTH: 11
<212> TYPE: PRT
<213> ORGANISM: Arabidopsis thaliana

<400> SEQUENCE: 16

Asp Leu Asp Leu Glu Leu Arg Leu Gly Phe Ala
  1               5                  10

<210> SEQ ID NO 17
<211> LENGTH: 12
<212> TYPE: PRT
<213> ORGANISM: Arabidopsis thaliana

<400> SEQUENCE: 17

Leu Asp Leu Asp Leu Glu Leu Arg Leu Gly Phe Ala
  1               5                  10

<210> SEQ ID NO 18
<211> LENGTH: 204
<212> TYPE: PRT
<213> ORGANISM: Arabidopsis thaliana

<400> SEQUENCE: 18

Met Glu Arg Ser Asn Ser Ile Glu Leu Arg Asn Ser Phe Tyr Gly Arg
  1               5                  10                  15

Ala Arg Thr Ser Pro Trp Ser Tyr Gly Asp Tyr Asp Asn Cys Gln Gln
             20                  25                  30

Asp His Asp Tyr Leu Leu Gly Phe Ser Trp Pro Pro Arg Ser Tyr Thr
         35                  40                  45

Cys Ser Phe Cys Lys Arg Glu Phe Arg Ser Ala Gln Ala Leu Gly Gly
     50                  55                  60

His Met Asn Val His Arg Arg Asp Arg Ala Arg Leu Arg Leu Gln Gln
 65                  70                  75                  80

Ser Pro Ser Ser Ser Thr Pro Ser Pro Tyr Pro Asn Pro Asn
             85                  90                  95

Tyr Ser Tyr Ser Thr Met Ala Asn Ser Pro Pro His His Ser Pro
            100                 105                 110

Leu Thr Leu Phe Pro Thr Leu Ser Pro Pro Ser Ser Pro Arg Tyr Arg
            115                 120                 125

Ala Gly Leu Ile Arg Ser Leu Ser Pro Lys Ser Lys His Thr Pro Glu
        130                 135                 140

Asn Ala Cys Lys Thr Lys Lys Ser Ser Leu Leu Val Glu Ala Gly Glu
145                 150                 155                 160

Ala Thr Arg Phe Thr Ser Lys Asp Ala Cys Lys Ile Leu Arg Asn Asp
                165                 170                 175

Glu Ile Ile Ser Leu Glu Leu Glu Ile Gly Leu Ile Asn Glu Ser Glu
            180                 185                 190

Gln Asp Leu Asp Leu Glu Leu Arg Leu Gly Phe Ala
        195                 200

<210> SEQ ID NO 19
<211> LENGTH: 30
<212> TYPE: PRT
<213> ORGANISM: Arabidopsis thaliana
```

```
<400> SEQUENCE: 19

Asn Asp Glu Ile Ile Ser Leu Glu Leu Glu Ile Gly Leu Ile Asn Glu
  1               5                  10                  15

Ser Glu Gln Asp Leu Asp Leu Glu Leu Arg Leu Gly Phe Ala
             20                  25                  30

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence:Amino Acid
      sequence, included in formula(I)

<400> SEQUENCE: 20

Leu Asp Leu Asn Leu
  1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence:Amino Acid
      sequence, included in formula(I)

<400> SEQUENCE: 21

Leu Asp Leu Glu Leu
  1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:Amino Acid
      sequence, included in formula(II)

<400> SEQUENCE: 22

Phe Asp Leu Asn Phe
  1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence:Amino Acid
      sequence, included in formula(II)

<400> SEQUENCE: 23

Phe Asp Leu Asn Ile
  1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:Amino Acid
      sequence, included in formula(III)

<400> SEQUENCE: 24

Leu Asp Leu Glu Leu Arg Leu
  1               5

<210> SEQ ID NO 25
```

```
<211> LENGTH: 7
<212> TYPE: PRT
<213> ORGANISM: Artificial Sequence
<220> FEATURE:
<223> OTHER INFORMATION: Description of Artificial Sequence:Amino Acid
      sequence, included in formula(III)

<400> SEQUENCE: 25

Leu Asp Leu Gln Leu Arg Leu
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:Amino Acid
      sequence, included in formula(III)

<400> SEQUENCE: 26

Leu Asp Leu Asp Leu Arg Leu
  1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:Amino Acid
      sequence, included in formula(III)

<400> SEQUENCE: 27

Asp Leu Asp Leu Glu Leu Arg Leu
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:Amino Acid
      sequence, included in formula(III)

<400> SEQUENCE: 28

Asp Leu Asp Leu Gln Leu Arg Leu
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:Amino Acid
      sequence, included in formula(III)

<400> SEQUENCE: 29

Asp Leu Asp Leu Asp Leu Arg Leu
  1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence:Amino Acid
      sequence, included in formula(III)

<400> SEQUENCE: 30

Leu Asp Leu Asp Leu Glu Leu Arg Leu
```

```
<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:Amino Acid
      sequence, included in formula(III)

<400> SEQUENCE: 31

Leu Asp Leu Asp Leu Gln Leu Arg Leu
 1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:Amino Acid
      sequence, included in formula(III)

<400> SEQUENCE: 32

Leu Asp Leu Asp Leu Asp Leu Arg Leu
 1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence:Amino Acid
      sequence, included in formula(IV)

<400> SEQUENCE: 33

Asp Leu Gln Leu Arg Leu
 1               5

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 34
cgatcttgat cttaaccttg ctccacctat ggaattttga g                        41

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 35
tcgactcaaa attccatagg tggagcaagg ttaagatcaa gatcg                    45

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 36
```

```
gggcttgatc ttaaccttgc tccacctatg gaattttgag                             40
```

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 37

```
tcgactcaaa attccatagg tggagcaagg ttaagatcaa gccc                       44
```

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 38

```
gggcttgatc ttaaccttgc tgctgctgct gctgcttgag                             40
```

<210> SEQ ID NO 39
<211> LENGTH: 44
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 39

```
tcgactcaag cagcagcagc agcagcaagg ttaagatcaa gccc                       44
```

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 40

```
gggctggatc tagaactccg tttgggtttc gcttaag                                37
```

<210> SEQ ID NO 41
<211> LENGTH: 41
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 41

```
tcgacttaag cgaaacccaa acggagttct agatccagcc c                           41
```

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 42

```
ggggatctag aactccgttt gtaatgag                                          28
```

```
<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 43
tcgactcatt acaaacggag ttctagatcc cc                                    32

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 44
gggctggatc tacaatccgt ttgggttatt actaatgag                             39

<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 45
tcgactcatt agtaataacc caaacggagt tgtagatcca ccc                        43

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 46
gggctggatc tagaactccg tttgtaatga g                                     31

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 47
tcgactcatt acaaacggag ttctagatcc agccc                                 35

<210> SEQ ID NO 48
<211> LENGTH: 43
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 48
gggctggatc tagaactcgc tgccgcagcg gctgcataat gag                        43
```

<210> SEQ ID NO 49
<211> LENGTH: 48
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 49
tcgactcatt atgcagccgc tgcggcagcg agttctagat ccagtccc                    48

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 50
gggctggatc tagaactccg tttggctgcc gcataatgag                             40

<210> SEQ ID NO 51
<211> LENGTH: 44
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 51
tcgactcatt atgcggcagc caaacggagt tctagatcca gccc                        44

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 52
gggctggatc tagaactccg tggttaag                                          28

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 53
tcgacttaac cacggagttc tagatccagc cc                                     32

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 54
gggttcgatc ttaattttgc accgttggat tgtgtttaag                             40

<210> SEQ ID NO 55
<211> LENGTH: 47

<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 55
tcgactcatt aaacacaatc caacggtgca aaattaagat cgaaccc          47

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 56
ggggacctca acatccctcc gatccctgaa ttctaag                     37

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 57
tcgacttaga attcagggat cggagggatg ttgaggtccc c                41

<210> SEQ ID NO 58
<211> LENGTH: 46
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 58
gggtttgaat tcgatcttaa ttttccaccg ttggattgtg tttaag           46

<210> SEQ ID NO 59
<211> LENGTH: 50
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 59
tcgacttaaa cacaatccaa cggtggaaaa ttaagatcga attcaaaccc       50

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 60
ggggatctag atctccgttt gtaatgag                               28

<210> SEQ ID NO 61
<211> LENGTH: 32
<212> TYPE: DNA
<213> ORGANISM: Artificial Sequence

```
<220> FEATURE:
<223> OTHER INFORMATION: Description of Artificial Sequence:Artificially
      Synthesized DNA Seqence

<400> SEQUENCE: 61
tcgactcatt acaaacggag atctagatcc cc                                    32

<210> SEQ ID NO 62
<211> LENGTH: 113
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 62
ggggtgggtc ctactgtgtc ggactcgtcc tctgcagtgg aagagaacca atatgatggg      60
gaaaagagga attgatcttg atcttaacct tgctccacct atggaatttt gag            113

<210> SEQ ID NO 63
<211> LENGTH: 118
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 63
tcgactcaaa attccatagg tggagcaagg ttaagatcaa gatcaattcc tcttttcccc      60
catcatattg gttctcttcc actgcagagg acgagtccga cacagtagga cccacccc      118

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 64
ggggatctgg atctagaact ccgtttgggt ttcgcttaag                            40

<210> SEQ ID NO 65
<211> LENGTH: 44
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 65
tcgacttaag cgaaacccaa acggagttct agatccagat cccc                       44

<210> SEQ ID NO 66
<211> LENGTH: 43
<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 66
gggcttgatc tggatctaga actccgtttg gtttcgctt aag                         43

<210> SEQ ID NO 67
<211> LENGTH: 47
```

<212> TYPE: DNA
<213> ORGANISM: Artificial Sequence
<220> FEATURE:
<223> OTHER INFORMATION: Description of Artificial Sequence:Artificially
      Synthesized DNA Seqence

<400> SEQUENCE: 67
tcgacttaag cgaaacccaa acggagttct agatccagat caagccc                      47

<210> SEQ ID NO 68
<211> LENGTH: 615
<212> TYPE: DNA
<213> ORGANISM: Arabidopsis thaliana

<400> SEQUENCE: 68
atggagagat caaacagcat agagttgagg aacagcttct atggccgtgc aagaacttca        60
ccatggagct atggagatta tgataattgc aacaggatc atgattatct tctagggttt       120
tcatggccac caagatccta cacttgcagc ttctgcaaaa gggaattcag atcggctcaa       180
gcacttggtg gccacatgaa tgttcacaga agagacagag caagactcag attacaacag       240
tctccatcat catcttcaac accttctcct ccttaccc ta accctaatta ctcttactca       300
accatggcaa actctcctcc tcctcatcat tctcctctaa ccctatttcc aacccttct       360 cctccatcct caccaagata tagggcaggt ttgatccgtt ccttgagccc caagtcaaaa       420
catacaccag aaaacgcttg taagactaag aaatcatctc ttttagtgga ggctggagag       480
gctacaaggt tcaccagtaa agatgcttgc aagatcctga ggaatgatga atcatcagc       540 ttggagcttg agattggttt gattaacgaa tcagagcaag atctggatct agaactccgt       600 ttgggttttcg cttaa                                                       615

<210> SEQ ID NO 69
<211> LENGTH: 93
<212> TYPE: DNA
<213> ORGANISM: Arabidopsis thaliana

<400> SEQUENCE: 69
aatgatgaaa tcatcagctt ggagcttgag attggtttga ttaacgaatc agagcaagat        60
ctggatctag aactccgttt gggtttcgct taa                                     93

<210> SEQ ID NO 70
<211> LENGTH: 218
<212> TYPE: PRT
<213> ORGANISM: Arabidopsis thaliana

<400> SEQUENCE: 70

Met Asp Pro Phe Leu Ile Gln Ser Pro Phe Ser Gly Phe Ser Pro Glu
  1               5                  10                  15

Tyr Ser Ile Gly Ser Ser Pro Asp Ser Phe Ser Ser Ser Ser Ser Asn
                 20                  25                  30

Asn Tyr Ser Leu Pro Phe Asn Glu Asn Asp Ser Glu Glu Met Phe Leu
             35                  40                  45

Tyr Gly Leu Ile Glu Gln Ser Thr Gln Gln Thr Tyr Ile Asp Ser Asp
         50                  55                  60

Ser Gln Asp Leu Pro Ile Lys Ser Val Ser Ser Arg Lys Ser Glu Lys
 65                  70                  75                  80

Ser Tyr Arg Gly Val Arg Arg Pro Trp Gly Lys Phe Ala Ala Glu
                 85                  90                  95

Ile Arg Asp Ser Thr Arg Asn Gly Ile Arg Val Trp Leu Gly Thr Phe
                100                 105                 110

Glu Ser Ala Glu Glu Ala Ala Leu Ala Tyr Asp Gln Ala Ala Phe Ser
        115                 120                 125

Met Arg Gly Ser Ser Ala Ile Leu Asn Phe Ser Ala Glu Arg Val Gln
130                 135                 140

Glu Ser Leu Ser Glu Ile Lys Tyr Thr Tyr Glu Asp Gly Cys Ser Pro
145                 150                 155                 160

Val Val Ala Leu Lys Arg Lys His Ser Met Arg Arg Met Thr Asn
            165                 170                 175

Lys Lys Thr Lys Asp Ser Asp Phe Asp His Arg Ser Val Lys Leu Asp
                180                 185                 190

Asn Val Val Phe Glu Asp Leu Gly Glu Gln Tyr Leu Glu Glu Leu
            195                 200                 205

Leu Gly Ser Ser Glu Asn Ser Gly Thr Trp
        210                 215

<210> SEQ ID NO 71
<211> LENGTH: 1098
<212> TYPE: DNA
<213> ORGANISM: Arabidopsis thaliana

<400> SEQUENCE: 71
atgatgtcaa aatctatgag catatcagtg aacggacaat ctcaagtgcc tcctgggttt      60
aggtttcatc cgaccgagga agagctgttg cagtattatc tccggaagaa agttaatagc     120
atcgagatcg atcttgatgt cattcgcgac gttgatctca acaagctcga gccttgggac     180
attcaagaga tgtgtaaaat aggaacaacg ccacaaaacg actggtattt ctttagccac     240
aaggacaaaa aatatccgac gggaacgaga actaacagag ccactgcggc tggattttgg     300
aaagcaactg gccgcgacaa gatcatatat agcaatggcc gtagaattgg gatgagaaag     360
actcttgttt tctacaaagg ccgagctcct cacggccaaa aatctgattg gatcatgcat     420
gaatatagac tcgatgacaa cattattttcc cccgaggatg tcaccgttca tgaggtcgtg     480
agtattatag gggaagcatc acaagacgaa ggatgggtgg tgtgtcgtat tttcaagaag     540
aagaatcttc acaaaaccct aaacagtccc gtcggaggag cttccctgag cggcggcgga     600
gatacgccga agacgacatc atctcagatc ttcaacgagg atactctcga ccaatttctt     660
gaacttatgg ggagatcttg taagaagag ctaaatcttg acccttttcat gaaactccca     720
aacctcgaaa gccctaacag tcaggcaatc aacaactgcc acgtaagctc tcccgacact     780
aatcataata tccacgtcag caacgtggtc gacactagct tgttactag ctgggcggct     840
ttagaccgcc tcgtggcctc gcagcttaac ggacccacat catattcaat tacagccgtc     900
aatgagagcc acgtgggcca tgatcatctc gctttgcctt ccgtccgatc tccgtacccc     960
agcctaaacc ggtccgcttc gtaccacgcc ggtttaacac aggaatatac accggagatg    1020
gagctatgga atacgacgac gtcgtctcta tcgtcatcgc ctggcccatt ttgtcacgtg    1080
tcgaatggta gtggataa                                                  1098

<210> SEQ ID NO 72
<211> LENGTH: 365
<212> TYPE: PRT
<213> ORGANISM: Arabidopsis thaliana

<400> SEQUENCE: 72

Met Met Ser Lys Ser Met Ser Ile Ser Val Asn Gly Gln Ser Gln Val
1               5                   10                  15

Pro Pro Gly Phe Arg Phe His Pro Thr Glu Glu Glu Leu Leu Gln Tyr

```
                    20                  25                  30
Tyr Leu Arg Lys Lys Val Asn Ser Ile Glu Ile Asp Leu Asp Val Ile
             35                  40                  45

Arg Asp Val Asp Leu Asn Lys Leu Glu Pro Trp Asp Ile Gln Glu Met
 50                  55                  60

Cys Lys Ile Gly Thr Thr Pro Gln Asn Asp Trp Tyr Phe Phe Ser His
 65                  70                  75                  80

Lys Asp Lys Lys Tyr Pro Thr Gly Thr Arg Thr Asn Arg Ala Thr Ala
                 85                  90                  95

Ala Gly Phe Trp Lys Ala Thr Gly Arg Asp Lys Ile Ile Tyr Ser Asn
            100                 105                 110

Gly Arg Arg Ile Gly Met Arg Lys Thr Leu Val Phe Tyr Lys Gly Arg
        115                 120                 125

Ala Pro His Gly Gln Lys Ser Asp Trp Ile Met His Glu Tyr Arg Leu
    130                 135                 140

Asp Asp Asn Ile Ile Ser Pro Glu Asp Val Thr Val His Glu Val Val
145                 150                 155                 160

Ser Ile Ile Gly Glu Ala Ser Gln Asp Glu Gly Trp Val Val Cys Arg
                165                 170                 175

Ile Phe Lys Lys Lys Asn Leu His Lys Thr Leu Asn Ser Pro Val Gly
            180                 185                 190

Gly Ala Ser Leu Ser Gly Gly Asp Thr Pro Lys Thr Thr Ser Ser
        195                 200                 205

Gln Ile Phe Asn Glu Asp Thr Leu Asp Gln Phe Leu Glu Leu Met Gly
    210                 215                 220

Arg Ser Cys Lys Glu Glu Leu Asn Leu Asp Pro Phe Met Lys Leu Pro
225                 230                 235                 240

Asn Leu Glu Ser Pro Asn Ser Gln Ala Ile Asn Asn Cys His Val Ser
                245                 250                 255

Ser Pro Asp Thr Asn His Asn Ile His Val Ser Asn Val Val Asp Thr
            260                 265                 270

Ser Phe Val Thr Ser Trp Ala Ala Leu Asp Arg Leu Val Ala Ser Gln
        275                 280                 285

Leu Asn Gly Pro Thr Ser Tyr Ser Ile Thr Ala Val Asn Glu Ser His
    290                 295                 300

Val Gly His Asp His Leu Ala Leu Pro Ser Val Arg Ser Pro Tyr Pro
305                 310                 315                 320

Ser Leu Asn Arg Ser Ala Ser Tyr His Ala Gly Leu Thr Gln Glu Tyr
                325                 330                 335

Thr Pro Glu Met Glu Leu Trp Asn Thr Thr Thr Ser Ser Leu Ser Ser
            340                 345                 350

Ser Pro Gly Pro Phe Cys His Val Ser Asn Gly Ser Gly
        355                 360                 365

<210> SEQ ID NO 73
<211> LENGTH: 1077
<212> TYPE: DNA
<213> ORGANISM: Arabidopsis thaliana

<400> SEQUENCE: 73
atggctgata taaggtcaa tctttcgatt aatggacaat caaaagtgcc tccaggtttc      60
agattccatc ccaccgaaga agaacttctc cattactatc tccgtaagaa agttaactct     120
caaaagatcg atcttgatgt cattcgtgaa gttgatctaa acaagcttga gccttgggat     180
attcaagagg aatgtagaat cggttcaacg ccacaaaacg actggtactt cttcagccac     240
```

```
aaggacaaga agtatccaac cgggaccagg acgaaccggg caacagtcgc tggattctgg    300
aaagctaccg gacgtgacaa aatcatctgc agttgtgtcc ggagaattgg actgaggaag    360
acactcgtgt tctacaaagg aagagctcct cacggtcaga atccgactg  gatcatgcat    420 gagtatcgcc tcgacgatac tccaatgtct aatggctatg ctgatgttgt tacagaagat    480
ccaatgagct ataacgaaga aggttgggtg gtatgtcgag tgttcaggaa gaagaactat    540
caaaagattg acgattgtcc taaaatcact ctatcttctt tacctgatga cacggaggaa    600
gagaaggggc ccacctttca acacactcaa aacgttaccg gtttagacca tgttcttctc    660
tacatggacc gtaccggttc taacatttgc atgcccgaga gccaaacaac gactcaacat    720
caagatgatg tcttattcat gcaactccca agtcttgaga cacctaaatc cgagagcccg    780
gtcgaccaaa gtttcctgac tccaagcaaa ctcgatttct ctcccgttca agagaagata    840
accgaaagac cggtttgcag caactgggct agtcttgacc ggctcgtagc ttggcaattg    900
aacaatggtc atcataatcc gtgtcatcgt aagagttttg atgaagaaga agaaaatggt    960
gatactatga tgcagcgatg ggatcttcat tggaataatg atgataatgt tgatctttgg   1020
agtagtttca ctgagtcttc ttcgtcttta gacccacttc ttcatttatc tgtatga      1077
```

<210> SEQ ID NO 74
<211> LENGTH: 358
<212> TYPE: PRT
<213> ORGANISM: Arabidopsis thaliana

<400> SEQUENCE: 74

```
Met Ala Asp Asn Lys Val Asn Leu Ser Ile Asn Gly Gln Ser Lys Val
 1               5                  10                  15

Pro Pro Gly Phe Arg Phe His Pro Thr Glu Glu Leu Leu His Tyr
            20                  25                  30

Tyr Leu Arg Lys Lys Val Asn Ser Gln Lys Ile Asp Leu Asp Val Ile
         35                  40                  45

Arg Glu Val Asp Leu Asn Lys Leu Glu Pro Trp Asp Ile Gln Glu Glu
     50                  55                  60

Cys Arg Ile Gly Ser Thr Pro Gln Asn Asp Trp Tyr Phe Phe Ser His
 65                  70                  75                  80

Lys Asp Lys Lys Tyr Pro Thr Gly Thr Arg Thr Asn Arg Ala Thr Val
                 85                  90                  95

Ala Gly Phe Trp Lys Ala Thr Gly Arg Asp Lys Ile Ile Cys Ser Cys
            100                 105                 110

Val Arg Arg Ile Gly Leu Arg Lys Thr Leu Val Phe Tyr Lys Gly Arg
        115                 120                 125

Ala Pro His Gly Gln Lys Ser Asp Trp Ile Met His Glu Tyr Arg Leu
    130                 135                 140

Asp Asp Thr Pro Met Ser Asn Gly Tyr Ala Asp Val Val Thr Glu Asp
145                 150                 155                 160

Pro Met Ser Tyr Asn Glu Glu Gly Trp Val Val Cys Arg Val Phe Arg
                165                 170                 175

Lys Lys Asn Tyr Gln Lys Ile Asp Asp Cys Pro Lys Ile Thr Leu Ser
            180                 185                 190

Ser Leu Pro Asp Asp Thr Glu Glu Lys Gly Pro Thr Phe His Asn
        195                 200                 205

Thr Gln Asn Val Thr Gly Leu Asp His Val Leu Leu Tyr Met Asp Arg
    210                 215                 220

Thr Gly Ser Asn Ile Cys Met Pro Glu Ser Gln Thr Thr Thr Gln His
```

```
            225                 230                 235                 240
Gln Asp Asp Val Leu Phe Met Gln Leu Pro Ser Leu Glu Thr Pro Lys
                245                 250                 255

Ser Glu Ser Pro Val Asp Gln Ser Phe Leu Thr Pro Ser Lys Leu Asp
            260                 265                 270

Phe Ser Pro Val Gln Glu Lys Ile Thr Glu Arg Pro Val Cys Ser Asn
        275                 280                 285

Trp Ala Ser Leu Asp Arg Leu Val Ala Trp Gln Leu Asn Asn Gly His
    290                 295                 300

His Asn Pro Cys His Arg Lys Ser Phe Asp Glu Glu Glu Asn Gly
305                 310                 315                 320

Asp Thr Met Met Gln Arg Trp Asp Leu His Trp Asn Asn Asp Asn
                325                 330                 335

Val Asp Leu Trp Ser Ser Phe Thr Glu Ser Ser Ser Leu Asp Pro
            340                 345                 350

Leu Leu His Leu Ser Val
        355

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence:
      Artificially Synthesized DNA Seqence

<400> SEQUENCE: 75
atggttcacg tagtgggcca tc                                              22

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized DNA Seqence

<400> SEQUENCE: 76
caaaatcgag attgtgatgt aaaa                                            24

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized DNA Seqence

<400> SEQUENCE: 77
cggacaatct caagtgcctc c                                               21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized DNA Seqence

<400> SEQUENCE: 78
ttacggggcc tactcttttt c                                               21

<210> SEQ ID NO 79
```

<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized DNA Seqence

<400> SEQUENCE: 79
taaaccttga atgtcccaag g                                             21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized DNA Seqence

<400> SEQUENCE: 80
cgtattgttt gtagagccgt g                                             21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized DNA Seqence

<400> SEQUENCE: 81
gtctcgtcga gtcctaccac c                                             21

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence:Amino Acid
      Sequence, included in formula(II)

<400> SEQUENCE: 82

Phe Asp Leu Asn
  1

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 83
gatcttgatc ttaaccttgc tccacctatg gaattt                             36

<210> SEQ ID NO 84
<211> LENGTH: 36
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 84
aaattccata ggtggagcaa ggttaagatc aagatc                             36

<210> SEQ ID NO 85
<211> LENGTH: 33

```
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 85
cttgatctta accttgctcc acctatggaa ttt                                    33

<210> SEQ ID NO 86
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 86
aaattccata ggtggagcaa ggttaagatc aag                                    33

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 87
cttgatctta accttgctgc tgctgctgct gct                                    33

<210> SEQ ID NO 88
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 88
agcagcagca gcagcagcaa ggttaagatc aag                                    33

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 89
ctggatctag aactccgttt gggtttcgct                                        30

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 90
agcgaaaccc aaacggagtt ctagatccag                                        30

<210> SEQ ID NO 91
<211> LENGTH: 18
<212> TYPE: DNA
<213> ORGANISM: Artificial Sequence
```

```
<220> FEATURE:
<223> OTHER INFORMATION: Description of Artificial Sequence:Artificially
      Synthesized  DNA Sequence

<400> SEQUENCE: 91
gatctagaac tccgtttg                                                      18

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 92
caaacggagt tctagatc                                                      18

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 93
ctggatctac aactccgttt gggttattac                                         30

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 94
gtaataaccc aaacggagtt gtagatccag                                         30

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 95
ctggatctag aactccgttt g                                                  21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 96
caaacggagt tctagatcca g                                                  21

<210> SEQ ID NO 97
<211> LENGTH: 33
<212> TYPE: DNA
<213> ORGANISM: Artificial Sequence
<220> FEATURE:
<223> OTHER INFORMATION: Description of Artificial Sequence:Artificially
```

```
                       Synthesized  DNA Sequence

<400> SEQUENCE: 97
ctggatctag aactcgctgc cgcagcggct gca                                    33

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 98
tgcagccgct gcggcagcga gttctagatc cag                                    33

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 99
ctggatctag aactccgttt ggctgccgca                                        30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 100
tgcggcagcc aaacggagtt ctagatccag                                        30

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 101
ctggatctag aactccgttt gggt                                              24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 102
acccaaacgg agttctagat ccag                                              24

<210> SEQ ID NO 103
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized  DNA Sequence
```

```
<400> SEQUENCE: 103
ttcgatctta attttgcacc gttggattgt gtt                                33

<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 104
aacacaatcc aacggtgcaa aattaagatc gaa                                33

<210> SEQ ID NO 105
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 105
tttgacctca acatccctcc gatccctgaa ttc                                33

<210> SEQ ID NO 106
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 106
gaattcaggg atcggaggga tgttgaggtc aaa                                33

<210> SEQ ID NO 107
<211> LENGTH: 39
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 107
tttcaattcg atcttaattt tccaccgttg gattgtgtt                          39

<210> SEQ ID NO 108
<211> LENGTH: 39
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 108
aacacaatcc aacggtggaa aattaagatc gaattgaaa                          39

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 109
```

```
gatctagatc tccgtttg                                                     18

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 110
caaacggaga tctagatc                                                     18

<210> SEQ ID NO 111
<211> LENGTH: 105
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 111
gtgggtccta ctgtgtcgga ctcgtcctct gcagtggaag agaaccaata tgatgggaaa       60
agaggaattg atcttgatct taaccttgct ccacctatgg aattt                      105

<210> SEQ ID NO 112
<211> LENGTH: 105
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 112
aaattccata ggtggagcaa ggttaagatc aagatcaatt cctctttcc catcatattg        60 gttctcttcc actgcagagg acgagtccga cacagtagga cccac                     105

<210> SEQ ID NO 113
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 113
gatctggatc tagaactccg tttggtttc gct                                     33

<210> SEQ ID NO 114
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 114
agcgaaaccc aaacggagtt ctagatccag atc                                    33

<210> SEQ ID NO 115
<211> LENGTH: 36
<212> TYPE: DNA
<213> ORGANISM: Artificial Sequence
<220> FEATURE:
<223> OTHER INFORMATION: Description of Artificial Sequence:Artificially
      Synthesized  DNA Sequence
```

```
<400> SEQUENCE: 115
cttgatctgg atctagaact ccgtttgggt ttcgct                                36

<210> SEQ ID NO 116
<211> LENGTH: 36
<212> TYPE: DNA
<213> ORGANISM: Artificial Sequence
<220> FEATURE:
<223> OTHER INFORMATION: Description of Artificial Sequence:Artificially
      Synthesized  DNA Sequence

<400> SEQUENCE: 116
agcgaaaccc aaacggagtt ctagatccag atcaag                                36

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 117

Asp Leu Asn Leu Arg Leu
 1               5

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 118
gatctaaacc tccgtctg                                                    18

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 119
cagacggagg tttagatc                                                    18

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 120

Asp Leu Asp Leu Arg Leu
 1               5

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 121
gatctagacc tccgtctg                                                 18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 122
cagacggagg tctagatc                                                 18

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 123

Asp Leu Gln Leu Arg Leu
 1               5

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 124
gatctacagc tccgtctg                                                 18

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 125
cagacggagc tgtagatc                                                 18

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 126

Asp Leu Arg Leu Arg Leu
 1               5

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 127
gatctacgac tccgtttg                                               18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 128
caaacggagt cgtagatc                                               18

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 129

Glu Leu Glu Leu Arg Leu
  1               5

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 130
gagctagaac tccgtttg                                               18

<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 131
caaacggagt tctagctc                                               18

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 132

Asn Leu Glu Leu Arg Leu
  1               5

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 133
aacctagaac tccgtttg                                                    18

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 134
caaacggagt tctaggtt                                                    18

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 135

Gln Leu Glu Leu Arg Leu
  1               5

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 136
cagctagaac tccgtttg                                                    18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 137
caaacggagt tctagctg                                                    18

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 138

Asp Leu Glu Leu Asn Leu
  1               5

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 139
gatctagaac tcaacttg                                                18

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 140
caagttgagt tctagatc                                                18

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 141

Asp Leu Glu Leu Gln Leu
 1               5

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 142
gatctagaac tccagttg                                                18

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 143
caactggagt tctagatc                                                18

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 144

Thr Leu Glu Leu Arg Leu
 1               5

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 145
acgcttgaat taagactc                                               18

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 146
gagtcttaat tcaagcgt                                               18

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 147

Asp Leu Glu Leu Thr Leu
  1               5

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 148
gatcttgaat taacgctc                                               18

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 149
gagcgttaat tcaagatc                                               18

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 150

Ser Leu Glu Leu Arg Leu
  1               5

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 151
agccttgaat taagactc                                                18

<210> SEQ ID NO 152
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 152
gagtcttaat tcaaggct                                                18

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 153

Asp Leu Glu Leu Ser Leu
 1               5

<210> SEQ ID NO 154
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 154
gatcttgaat taagcctc                                                18

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 155
gaggcttaat tcaagatc                                                18

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 156

Asp Leu Thr Leu Arg Leu
 1               5

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 157
gatcttacct taagactc                                                18

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 158
gagtcttaag gtaagatc                                                18

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 159

Asp Leu Ser Leu Arg Leu
 1               5

<210> SEQ ID NO 160
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 160
gatcttagct taagactc                                                18

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 161
gagtcttaag ctaagatc                                                18

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 162

Asp Leu His Leu Arg Leu
 1               5

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 163
gatcttcact taagactc                                                 18

<210> SEQ ID NO 164
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 164
gagtcttaag tgaagatc                                                 18

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 165

Asp Leu Glu Phe Arg Leu
 1               5

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 166
gatctcgaat ttcgtctc                                                 18

<210> SEQ ID NO 167
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 167
gagacgaaat tcgagatc                                                 18

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 168

Asp Phe Glu Leu Arg Leu
 1               5

<210> SEQ ID NO 169
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 169
gatttcgaac tacgtctc                                                18

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 170
gagacgtagt tcgaaatc                                                18

<210> SEQ ID NO 171
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 171

Ser Leu Asp Leu His Leu
 1               5

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 172
tcgcttgatc tacacctg                                                18

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 173
caggtgtaga tcaagcga                                                18

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 174

Asp Leu Thr Leu Lys Leu
 1               5

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 175
gatcttacgc taaagctg                                                 18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 176
cagctttagc gtaagatc                                                 18

<210> SEQ ID NO 177
<211> LENGTH: 6
<212> TYPE: PRT
<213> ORGANISM: Artificial Sequence
<220> FEATURE:
<223> OTHER INFORMATION: Description of Artificial Sequence:Artificially
      Synthesized Amino Acid Sequence

<400> SEQUENCE: 177

Asp Leu Ser Leu Lys Leu
  1               5

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 178
gatcttagcc taaagctg                                                 18

<210> SEQ ID NO 179
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 179
cagctttagg ctaagatc                                                 18
```